United States Patent

Frei et al.

(10) Patent No.: US 8,613,900 B2
(45) Date of Patent: Dec. 24, 2013

(54) NANOSTRUCTURED TRANSITION METAL OXIDES USEFUL FOR WATER OXIDATION CATALYSIS

(75) Inventors: Heinz M. Frei, Berkeley, CA (US); Feng Jiao, Newark, DE (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/575,829

(22) PCT Filed: Jan. 27, 2011

(86) PCT No.: PCT/US2011/022789
§ 371 (c)(1),
(2), (4) Date: Sep. 11, 2012

(87) PCT Pub. No.: WO2011/094456
PCT Pub. Date: Aug. 4, 2011

(65) Prior Publication Data
US 2012/0328505 A1    Dec. 27, 2012

Related U.S. Application Data

(60) Provisional application No. 61/298,876, filed on Jan. 27, 2010.

(51) Int. Cl.
*C01B 13/14*    (2006.01)
(52) U.S. Cl.
USPC ........ 423/592.1; 423/579; 502/324; 502/240; 502/338; 502/305; 502/300; 502/325
(58) Field of Classification Search
USPC ................. 502/325, 324, 240, 338, 305, 300; 423/579, 592.1
See application file for complete search history.

(56) References Cited

FOREIGN PATENT DOCUMENTS

WO    WO 2008102351 A2  *  8/2008

OTHER PUBLICATIONS

Karla R. Reyes Gil; Joshua M. Spurgeon; Nathan S. Lewis, Silicon and Tungsten oxide nanostructures for water splitting, Aug. 20, 2009, Solar Hydrogen and Nanotechnology IV, vol. 7408, p. 74080S-1 to 74080S-11.*
Wenfeng Shangguan; Kozo Inoue, Synthesis of silica-pillared layered titanium niobium oxide, Jan. 1, 1998, RSC Publishing, p. 779-780.*
Anne Galarneau, Hélène Cambon, Thierry Martin, Louis-Charles De Ménorval, Daniel Brunel, Francesco Di Renzo, François Fajula "SBA-15 versus MCM-41: are they the same materials?" Studies in Surface Science and Catalysis, vol. 141, 2002, pp. 395-402.*
Hongxian Han, Heinz Frei "Visiblelightabsorption of binuclear TiOCoII charge-transfer unit assembled in mesoporoussilica" Microporous and Mesoporous Materials, vol. 103, Issues 1-3, Jun. 20, 2007, pp. 265-272.*

* cited by examiner

*Primary Examiner* — Colleen Dunn
*Assistant Examiner* — Haytham Soliman
(74) *Attorney, Agent, or Firm* — Lawrence Berkeley National Laboratory

(57) ABSTRACT

The present invention provides for a composition comprising a nanostructured transition metal oxide capable of oxidizing two $H_2O$ molecules to obtain four protons. In some embodiments of the invention, the composition further comprises a porous matrix wherein the nanocluster of the transition metal oxide is embedded on and/or in the porous matrix.

13 Claims, 12 Drawing Sheets

NANOSTRUCTURED TRANSITION METAL OXIDES USEFUL FOR WATER OXIDATION CATALYSIS

RELATED PATENT APPLICATIONS

This application claims priority to PCT Application PCT/US2011/022789, filed Jan. 27, 2011, which in turn claims priority to U.S. Provisional Patent Application Ser. No. 61/298,876, filed Jan. 27, 2010, which application is incorporated herein by reference as if fully set forth in its entirety.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of catalytic water oxidation.

BACKGROUND OF THE INVENTION

Currently there is no artificial photosynthetic system that converts carbon dioxide and water with sunlight to a liquid fuel. Such a system needs to be sufficiently efficient for keeping up with the incident flux of solar photons, must be durable, made of Earth abundant materials and with scalable synthetic methods.

Currently the scientific community is investigating the specific problem of efficient catalytic water oxidation, which is a mandatory step of any sunlight to fuel conversion system, by exploring molecular organometallic catalysts or by using electrocatalytic metal oxide deposits in electrochemical cell configurations. The best available molecular catalysts using Earth abundant metals are still far too slow for keeping up with the solar flux, and are unstable. Metal oxide layers of abundant elements deposited onto various metal anodes, especially metal oxides of Co and Mn, are known to catalyze water oxidation typically under harsh (very basic) pH conditions.

SUMMARY OF THE INVENTION

The present invention provides for a composition comprising a nanostructured transition metal oxide. The nanostructured transition metal oxide can be in a nanocluster. The nanostructured transition metal oxide is capable of oxidizing two $H_2O$ molecules to obtain four protons. In some embodiments, the nanostructure is a nanorod. In some embodiments, the nanocluster is a bundle of parallel nanorods. In some embodiments, two or more nanorods of the bundle of parallel nanorods are interconnected to each other by short bridges. In some embodiments, each nanorod has a diameter of from about 6 nm to about 10 nm. In some embodiments, each nanorod has a diameter of about 8 nm. In some embodiments, the length of the nanorods is from about 40 nm to about 60 nm. In some embodiments, each bundle has a spheroid shape with a small diameter of from 20 nm to about 50 nm, and a long diameter of from 50 nm to about 200 nm. In some embodiments, each bundle has a spheroid shape with a small diameter of from 30 nm to about 40 nm, and a long diameter of from 60 nm to about 100 nm. In some embodiments, the average length of the nanorods in a bundle of nanorods is from about 40 nm to about 60 nm. In some embodiments, when there is a plurality of nanoclusters, the bundles have an average short diameter from about 40 nm to about 80, and an average long diameter from about 60 nm to about 180 nm. In some embodiments, the nanocluster has a crystalline nature.

In some embodiments of the invention, the transition metal of the transition metal oxide is a Period 4, 5 or 6 transition metal. In some embodiments, the Period 4 transition metal is cobalt, iron, or manganese. In some embodiments, the Period 5 transition metal is nobelium. In some embodiments, the Period 6 transition metal is tungsten. In some embodiments, the transition metal oxide is $Co_3O_4$, $MnO_2$, $Mn_2O_3$, or $Mn_3O_4$. In some embodiments, within one nanorod or nanocluster, the transition metal oxide can comprise either only one transition metal element, or a mixture of two or more transition metal elements.

In some embodiments of the invention, the composition further comprises a porous matrix wherein the nanocluster of the transition metal oxide is embedded on and/or in the porous matrix. In some embodiments, the porous matrix is a mesoporous scaffold, such as a mesoporous silica scaffold. The porous matrix can act as a proton sponge to absorb protons produced by the catalysis of water. In some embodiments, the porous matrix is a KIT-6 nanopore or SBA-15.

The present invention also provides for a method of producing molecular oxygen from water comprising: (a) providing a composition comprising a nanostructured transition metal oxide of the present invention, and (b) contacting the water with the nanostructured transition metal oxide such that the nanostructured transition metal oxide catalyzes the water to produce molecular oxygen.

The present invention also provides for a device comprising the composition comprising a nanocluster of a transition metal oxide. The device can be a solar fuel device or a photoelectric device.

In some embodiments of the invention, the composition catalyzes the reaction:

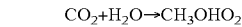

$$CO_2 + H_2O \rightarrow CH_3OHO_2$$

visible light with a turnover frequency (TOF) equal to or more than 1,000 $s^{-1}$ or 1,140 $s^{-1}$ per nanocluster.

In one aspect, the present invention provides for a Co and Mn oxide nanocluster catalysts supported on mesoporous silica scaffolds affords for the first time a visible light driven catalytic system for water oxidation to oxygen that is capable of keeping up with the solar flux, is robust, made of Earth abundant elements and with synthetic methods (hydrothermal synthesis, wet impregnation, calcination) that are suitable for scalable manufacturing.

In another aspect, the present invention provides for a viable system that oxidizes water to oxygen at a rate commensurate with the photon flux at high solar intensity. Water oxidation to oxygen with visible light is accomplished by Photosystem II of photosynthetic bacteria and plants. However, the natural systems are inefficient (at noon, 90% of the incident solar photons are converted to heat in order to avoid excessive damage to the protein environment) and fragile (under sunlight, the water oxidation catalyst complex needs to be replaced every 30 minutes, which takes 30 minutes). Noble metal clusters such as Ir oxide or Ru oxide are established water oxidation catalysts that are both efficient and robust, but these elements are scarce and, hence, the catalysts are not scalable and therefore not viable. Currently a few molecular water oxidation catalysts featuring abundant first row transition metals are known but are very inefficient and not robust. Co and Mn oxide layers deposited on anodes of electrochemical cells are known to act as water oxidation electrocatalysts.

In another aspect, the present invention overcomes the technical problem of packing a several orders of magnitude higher density of active Co or Mn sites than hitherto possible into a nanometer-sized, stable catalytic particle for water oxidation. Furthermore, the invention overcomes the existing assumption that efficient water oxidation catalysis requires a catalyst molecule or cluster performing at a rate commensurate with the solar flux. The invention demonstrates an alternative approach based on many catalysts (tens to hundreds) stacked in a robust inert support which, as an ensemble, achieve the required rate of 100 catalytic turnovers per second per square nanometer for keeping up with the flux of incident solar photons.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
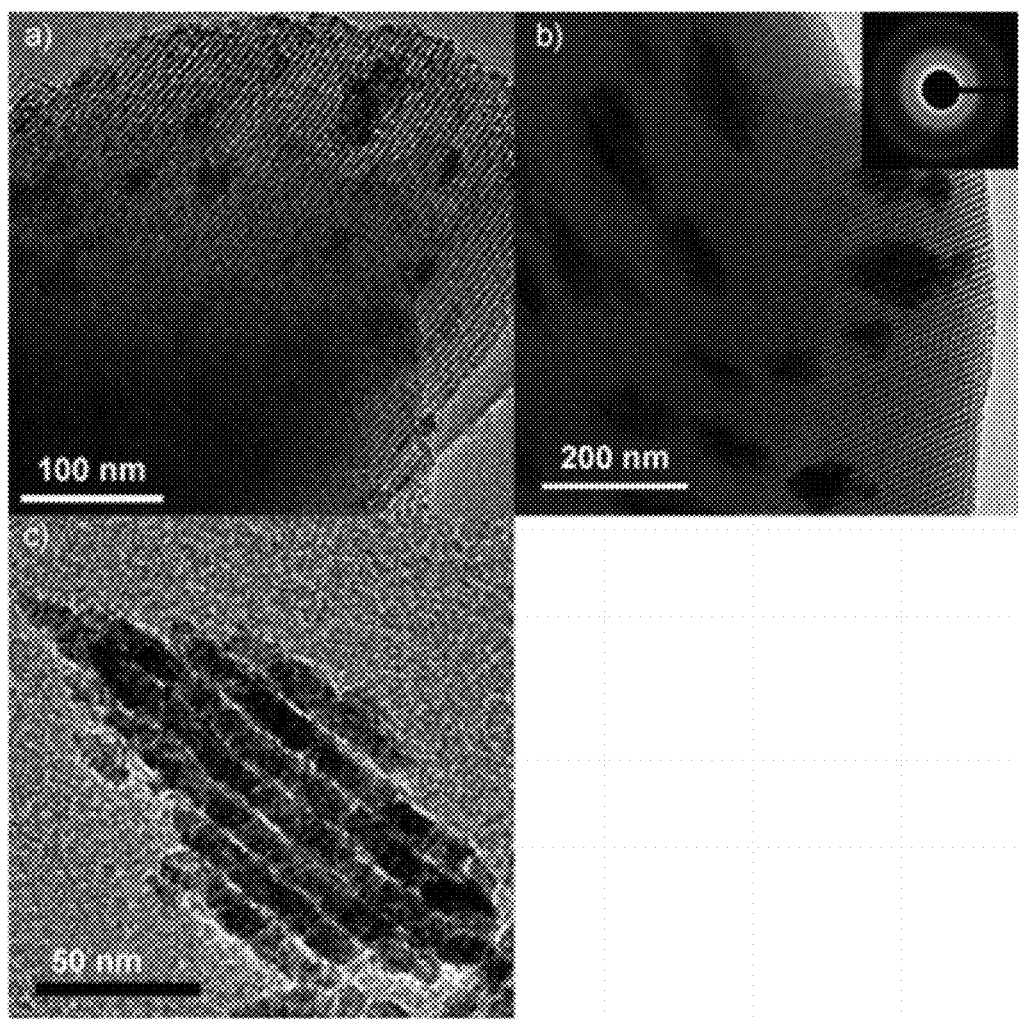
FIG. 1 shows the TEM images of a) SBA-15/$Co_3O_4$ 4% loading, b) SBA-15/$Co_3O_4$ 8% loading, c) $Co_3O_4$ nanocluster (8% sample) after removal of the SBA-15 silica material using aqueous NaOH as etching reagent. The inset in (b) shows the SAED pattern.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

As used in the specification and the appended claims, the singular forms "a", "an", and "the" include plural references unless the context clearly dictates otherwise. Thus, for example, reference to a "crystal" includes a single crystal as well as a plurality of crystals.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

These and other objects, advantages, and features of the invention will become apparent to those persons skilled in the art upon reading the details of the invention as more fully described below.

1. Transition Metal Oxide Nanocluster Catalyst in a Silica Scaffold

Using a wet impregnation method (using a transition metal salt, such as a nitrate, in ethanol, 4 wt % loading) followed by controlled calcination at a temperature from 250 to 900° C., such as 500° C., one can prepare about 35 nm sized transition metal oxide clusters inside a porous matrix, such as a mesoporous SBA-15 silica support. The clusters can comprise of parallel bundles of nanorods (such as 8 nm diameter) optionally interconnected by short bridge. The clusters inside the porous matrix can be such that the nanorod bundles are exact replicas of a SBA-15 mesopore structure, with about 8 nm channels giving rise to the nanorods and the micropores connecting the channels yielding the short bridges between rods. The nanorod bundles can have a spheroidal shape with a short diameter of about 35 nm and a long diameter of about 65 nm. A exemplary porous matrix is SBA-15 which is an established mesoporous silica support with a very high surface area and internal volume. The transitionmetal oxide can be in a spinel structure.

2. $Co_3O_4$ Nanocluster Catalyst in SBA-15 Silica Scaffold

Using a wet impregnation method ($Co(NO_3)_2$ in ethanol, 4 wt % loading) followed by controlled calcination at a temperature from 250 to 900° C., such as 500° C., we prepared 35 nm sized $Co_3O_4$ clusters inside mesoporous SBA-15 silica support. The clusters consist of parallel bundles of nanorods (8 nm diameter) interconnected by short bridges, as shown in FIG. 10A. Close inspection of the TEM (transmission electron microscope) images of the clusters inside the silica support, or in bare form obtained after removal of the silica by edging (FIG. 10Ac) shows that the nanorod bundles are exact replicas of the SBA-15 mesopore structure, with the 8 nm channels giving rise to the nanorods and the micropores connecting the channels yielding the short bridges between rods. The nanorod bundles have spheroidal shape with a short diameter of 35 nm and a long diameter of 65 nm. SBA-15 is an established mesoporous silica support with a very high surface area and internal volume. XRD (X-ray diffraction) and EXAFS spectra (extended X-ray absorption fine structure) confirmed the spinel structure of the $Co_3O_4$ catalysts (FIG. 10B).

An aqueous suspension (pH 5.8, room temperature) of the mesoporous silica particles (about one micrometer sized cubes) containing $Co_3O_4$ clusters was loaded with a light sensitizer complex ($Ru^{+2}(bpy)_3$ (bpy=bipyridine) and persulfate electron acceptor for driving the catalyst with visible light (wavelength 476 nm). Absorption of light by the sensitizer generated $Ru^{+3}(bpy)_3$ species capable of driving a multi-electron transfer catalyst for water oxidation (a standard technique for comparing efficiencies of various water oxidation catalysts). Rapid evolution of $O_2$ in the headspace of the aqueous solution was detected by mass spectrometric analysis, shown in FIG. 10C,D. Evolution of oxygen gas was linear during the first 20 minutes, then leveled off after one hour due to consumption of the persulfate acceptor. Production of oxygen resumed at the initial rate after adding fresh $S_2O_8^{-2}$ acceptor, thus confirming the stability of the catalyst. From these measurements, a turnover frequency of 1140 $s^{-1}$ per $Co_3O_4$ cluster was calculated (TOF (turnover frequency) is the number of oxygen molecules produced per second per nanocluster). The reaction proceeds under mild conditions of close to neutral pH (5.8) and temperature (22° C.), and modest overpotential (350 mV). Oxygen evolution at these nanostructured $Co_3O_4$ clusters in mesoporous silica constitutes the first observation of efficient water oxidation by a nanometer sized multi-electron catalyst made of an abundant transition metal oxide.

Comparison of the rates of $O_2$ production of nanostructured catalyst clusters and micron-sized $Co_3O_4$ particles (FIG. 10D), normalized to equal weight, furnishes insight into the factors responsible for the high catalytic efficiency. The nanoclusters are 1550 times more efficient than the micron-sized particles. The dominant contribution, namely a factor of 96 is due to the much larger surface area of the nanostructured cluster. Another factor of 16 reflects a higher activity of Co surface sites in the case of the nanocluster, very likely caused by the sharply curved nanorod surface and/or a synergistic effect of the Co oxide surface interacting with the silica wall environment. Taking the geometrical projection of the 35 nm diameter bundle of nanorods onto a plane, a TOF of one $O_2$ molecule $s^{-1} nm^{-2}$ is calculated. Therefore, a stack of one hundred of these $Co_3O_4$ clusters in a nanoporous silica scaffold, which is achieved in a pressed wafer of SBA-15/$Co_3O_4$ particles of mere 150 micrometer thickness, meets the required TOF of 100 $s^{-1} nm^{-2}$ for the water oxidation catalysis to keep up with the solar flux at high sunlight intensity. The high rate, mild pH and temperature conditions, modest overpotential, robustness and abundance of the material make this a promising catalyst for water oxidation in solar fuel generating systems.

3. Mn Oxide Nanocluster Catalyst in KIT-6 Silica Scaffold

Figure 11:
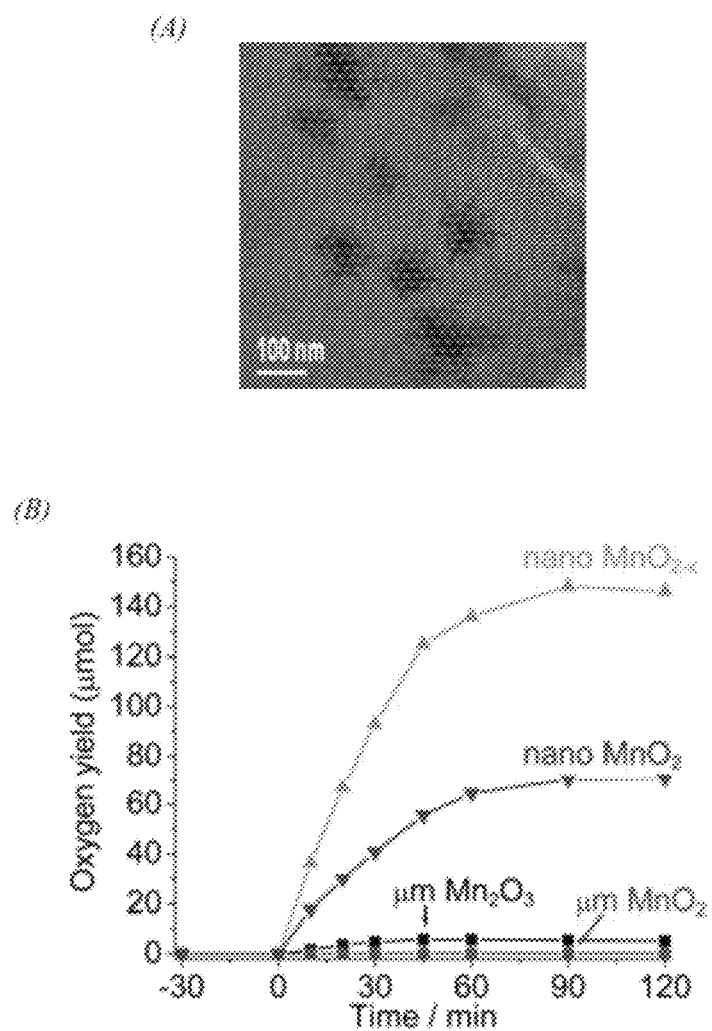
FIG. 11 shows the Mn oxide nanocluster catalyst for water oxidation in KIT-6 silica support. (A) TEM image of KIT-6/Mn oxide 6% loading, prepared by calcination at 600 C. (B) Mass spectrometric monitoring (mass 32) of visible light driven oxygen evolution of KIT-6/Mn oxide aqueous suspension: orange trace, Mn oxide clusters prepared by calcination at 600° C.; blue trace, Mn oxide clusters prepared by calcination at 400° C. Comparison with activity of $Mn_2O_3$ (black trace) and $MnO_2$ (red trace) bare micron sized particle suspensions is also shown.

A bisolvent wet impregnation method was employed for preparing highly nanostructured catalyst clusters of Mn oxide in mesoporous silica of type KIT-6. In a typical synthesis, 2 mL aqueous solution of $Mn(NO_3)_2 6H_2O$ was combined with a suspension of 2 g of mesoporous silica in 100 mL of dried n-hexane under stirring. After continuous stirring of the combined solution for 3 hours, it was filtered and the resulting powder thoroughly dried. Calcination at selected temperature between 400 and 900° C. for 3 hours provided the final catalyst product. The TEM images of FIG. 11A show the formation of approx. spherical nanoclusters of between 73 and 86 nm diameter depending on the selected calcination temperature (Mn oxide loading level 6.0±0.3% per ICP-MS measurement). The nanocluster size, which spanned a narrow range for each calcination temperature selected, was determined by examining the TEM image of hundreds of nanoparticles. The nanostructure of the clusters replicates the 3 dimensional network of 8 nm channels of KIT-6. The silica structure remained unperturbed by the impregnation procedure according to XRD and TEM data. Component analysis of the XANES spectra (X-ray absorption near edge structure, least squares fitting program SIXPACK) revealed that the atomic structure of the Mn oxide nanoclusters consisted mainly of three phases, namely $MnO_2$, $Mn_2O_3$, and $Mn_3O_4$. XANES spectra of micrometer sized particles of $\beta$-$MnO_2$, $\alpha$-$Mn_2O_3$, and $Mn_3O_4$ particles were used for Mn K-edge fitting. The fractional composition of the Mn oxide clusters depends on calcination temperature, and results are summarized in Table 3.

Using the $Ru^{+2}(bpy)_3$—persulfate sensitization system to drive the KIT-6 supported Mn oxide nanocluster catalyst in aqueous solution with visible light (476 nm), gaseous $O_2$ evolution was observed in the headspace of the suspension and analyzed quantitatively by mass spectrometry. FIG. 11B shows the buildup of $O_2$ product for materials prepared at various calcination temperatures between 400 and 900° C. The catalyst prepared at 600° C. exhibits the highest activity, corresponding to TOF of 3330 $s^{-1}$ per nanocluster. The dominant structural phase of the catalyst is $Mn_2O_3$ (80%), with smaller contributions from $Mn_3O_4$ (14%) and $MnO_2$ (6%). High stability of the catalyst was established by the following observations: Oxygen evolution continued at the same rate after replenishing the reaction solution with persulfate acceptor and maintaining a pH of 5.8. Leaching of Mn ions into solution upon prolonged photochemical water oxidation was very small ($4 \times 10^{-7}$ M per ICP measurement) and barely above the detection limit. Furthermore, recording of the K-edge by X-ray absorption spectroscopy of the catalyst before and after photolysis indicated no change of the Mn oxidation state. The result shows for the first time that efficient oxidation of water to $O_2$ can be accomplished with nanostructured Mn oxide cluster catalysts supported on mesoporous silica under mild conditions of temperature (22° C.) and pH (5.8), and with modest overpotential (350 mV). Mn is an Earth abundant and environmentally friendly metal and therefore particularly suited for large scale use.

The TOF per area when the Mn oxide nanocluster catalyst is projected on a plane is 0.6 $s^{-1}$ $nm^{-2}$. Therefore, stacking of two hundred nanoclusters in the mesoporous scaffold, which is readily achieved, affords a photocatalytic water oxidation system capable of keeping up with the solar flux. The nanoporous silica scaffolds plays a critical role for the integrity of the catalytic system by providing a high, stable dispersion of the Mn oxide clusters and by sustaining the catalytic activity by protecting the active Mn centers from deactivation by surface restructuring.

TABLE 3

Component analysis results for KIT-6/$MnO_x$ by least squares fitting function (SIXPACK software, S. Webb, SSRL).

|  | $MnO_2$ | $Mn_2O_3$ | $Mn_3O_4$ |
| --- | --- | --- | --- |
| 400° C. | 64% | 36% | — |
| 500° C. | 95% | 5% | — |
| 600° C. | 6% | 80% | 14% |
| 700° C. | — | 81% | 19% |
| 800° C. | — | 70% | 30% |
| 900° C. | — | 51% | 49% |

The present invention has application in the energy industry. Catalytic water oxidation with visible light is a mandatory step of any technology for making a liquid fuel from water and carbon dioxide (or hydrogen from water) because water is the only viable source of electrons. The critical role of water oxidation stems from the fact that consumption of any fuel for generating useful energy, either in a fuel cell or by direct combustion, is accompanied by the reduction of $O_2$ to water. Therefore, to close the solar fuel cycle, water is the only admissible electron source. The transitionmetal oxide nanocluster catalysts of the present invention can be incorporated in a variety of configurations and systems for sunlight to fuel conversion. The present invention also has application in the car industry and in solar fuels.

REFERENCES CITED

[1] http://rredc.nrel.gov/solar/spectra/am1.5.
[2] J. Kiwi, M. Gr"tzel, Angew. Chem. 1978, 90, 900; Angew. Chem. Int. Ed. Engl. 1978, 17, 860.
[3] J. M. Lehn, J. P. Sauvage, R. Ziessel, Nouv. J. Chim. 1980, 4, 355.
[4] A. Harriman, I. J. Pickering, J. M. Thomas, P. A. Christensen, J. Chem. Soc. Faraday Trans. 1 1988, 84, 2795.
[5] M. Hara, J. T. Lean, T. E. Mallouk, Chem. Mater. 2001, 13, 4668.
[6] N. D. Morris, M. Suzuki, T. E. Mallouk, J. Phys. Chem. A 2004, 108, 9115.
[7] P. G. Hoertz, Y. I. Kim, W. J. Youngblood, T. E. Mallouk, J. Phys. Chem. B 2007, 111, 6845.
[8] M. Yagi, E. Tomita, S. Sakita, T. Kuwabara, K. Nagai, J. Phys. Chem. B 2005, 109, 21489.
[9] H. Han, H. Frei, J. Phys. Chem. C 2008, 112, 16156.
[10] R. Nakamura, H. Frei, J. Am. Chem. Soc. 2006, 128, 10668.
[11] J. Yano, J. Kern, K. Sauer, M. J. Latimer, Y. Pushkar, J. Biesiadka, B. Loll, W. Saenger, J. Messinger, A. Zouni, V. K. Yachandra, Science 2006, 314, 821.
[12] See Example 2.
[13] T. Schmidt, H. Wendt, Electrochim. Acta 1994, 39, 1763.
[14] C. Iwakura, A. Honji, H. Tamura, Electrochim. Acta 1981, 26, 1319.
[15] P. Rasiyah, A. C. C. Tseung, J. Electrochem. Soc. 1983, 130, 365.
[16] R. N. Singh, D. Mishra, Anindita, A. S. K. Sinha, A. Singh, Electrochem. Commun. 2007, 9, 1369.
[17] M. W. Kanan, D. G. Nocera, Science 2008, 321, 1072.
[18] M. Morita, C. Iwakura, H. Tamura, Electrochim. Acta 1977, 22, 325.
[19] A. Kay, I. Cesar, M. Gr"tzel, J. Am. Chem. Soc. 2006, 128, 15714.
[20] D. Y. Zhao, J. L. Feng, Q. S. Huo, N. Melosh, G. H. Fredrickson, B. F. Chmelka, G. D. Stucky, Science 1998, 279, 548.
[21] F. Jiao, K. M. Shaju, P. G. Bruce, Angew. Chem. 2005, 117, 6708; Angew. Chem. Int. Ed. 2005, 44, 6550.
[22] B. Z. Tian, X. Y. Liu, H. F. Yang, S. H. Xie, C. Z. Yu, B. Tu, D. Y. Zhao, Adv. Mater. 2003, 15, 1370.
[23] K. Maeda, K. Teramura, D. L. Lu, N. Saito, Y. Inoue, K. Domen, J. Phys. Chem. C 2007, 111, 7554.
[24] M. Hara, C. C. Waraksa, J. T. Lean, B. A. Lewis, T. E. Mallouk, J. Phys. Chem. A 2000, 104, 5275.
[25] CRC Handbook of Chemistry and Physics, 85th ed. (Ed.: D. R. Lide), CRC, Boca Raton, Fla., 2004, pp. 8-27.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

The development of integrated artificial photosynthetic systems for the direct conversion of carbon dioxide and water to fuel depends on the availability of efficient and robust catalysts for the chemical transformations. Catalysts need to exhibit turnover frequency (TOF) and density (hence size) commensurate with the solar flux at ground level (1000 Wm$^{-2}$, airmass (AM) 1.5) [1] to avoid wasting of incident solar photons. For example, a catalyst with a TOF of 100 s$^{-1}$ requires a density of one catalytic site per square nanometer. Catalysts with lower rates or taking up a larger space will require a high-surface-area, nanostructured support that affords tens to hundreds of catalytic sites per square nanometer. Furthermore, catalysts need to operate close to the thermodynamic potential of the redox reaction so that a maximum fraction of the solar photon energy is converted to chemical energy. Stability considerations favor all-inorganic oxide materials, as does avoidance of harsh reaction conditions of pH value or temperature.

For the water oxidation half reaction, iridium oxide is a material that essentially fulfils these requirements. After early reports that identified IrO$_2$ particles as robust water oxidation catalysts, [2-4] Mallouk and co-workers determined a TOF for Ir oxide colloidal particles of 40 s$_{t1}$ in aqueous solution (pH 5.7, 25° C.). [5-7] In this work, the catalyst was driven by a [Ru$^{3+}$ (bpy)$_3$] unit (bpy=2,2'-bipyridine) generated photochemically with visible light using the established [Ru$^{2+}$ (bpy)$_3$]/persulfate system with a modest overpotential ($\eta$) of 370 mV. For IrO$_2$ colloidal particles coated on an indium tin oxide anode, Yagi et al. obtained TOF=7 s$^{-1}$ (pH 5.3, 25° C., $\eta$=570 mV) from electrochemical measurements.[8] We have recently demonstrated that all-inorganic photocatalytic units consisting of IrO$_2$ nanoclusters (ca. 2 nm) directly coupled to a single-center chromium(VI) or a binuclear TiCr$^{III}$ charge transfer chromophore afford oxygen evolution under visible light with good quantum yield. [9, 10] While iridium oxide closely approaches the efficiency and stability required for a water oxidation catalyst in a solar conversion system, iridium is the least abundant metal on earth and is not suitable for use on a very large scale. Therefore, it is imperative to explore oxides of the much more abundant first-row transition metals, as inspired by nature's Mn$_4$Ca cluster of photosystem II. [11] Herein, we focus on Co$_3$O$_4$ nanoclusters as candidates for water oxidation catalysts under mild conditions.

Numerous electrochemical studies of cobalt and manganese oxides as catalytic materials for oxygen evolution have been conducted over the past decades. For the purpose of evaluating metal oxides in the form of nanometer-sized clusters as catalytic components for water oxidation, comparisons of turnover frequencies are most relevant. Such values were typically not reported in electrochemical studies, but lower limits can be calculated in cases where the amount of catalyst material was indicated. The data are summarized in Table 1 of Example 2 ("lower limits" refers to the assumption that all deposited metal centers are catalytically active). [12] Briefly, for Co$_3$O$_4$ (spinel), lower limits of TOF ranging from 0.020 to 0.0008 s$^{-1}$ at high pH values and temperatures between 25 and 120° C. were derived from work by Schmidt, Iwakura, Rasiyah, and Singh et al. [13-16] Using an in situ activation method for developing a cobalt-based electrocatalytic film, [13] Kanan and Nocera reported very recently oxygen evolution from pH-neutral, phosphate-buffered aqueous solution for which a TOF≥0.0007 s$^{-1}$($\eta$=410 mV) is estimated. [12, 17] A study at neutral pH values and room temperature using an anode coated with MnO$_2$ by Morita et al. gave TOF≥0.013 s$^{-1}$ ($\eta$=440 mV). [18] Using silicon-doped nanostructured Fe$_2$O$_3$ topped by a Co monolayer as photocatalytic anode material, Grätzel reported high incident photon-to-current efficiency at negligible overpotential in photoelectrochemical water oxidation. [19] Furthermore, oxygen evolution was reported by Harriman et al. from aqueous suspensions of micrometer-sized Co$_3$O$_4$ or Mn$_2$O$_3$ particles using the photochemical [Ru$_{2+}$(bpy)$_3$]/persulfate method (pH 5, room temperature, $\eta$=325 mV). [4] Data presented in that study indicate TOF between 0.035 and 0.055 s$_{t1}$. The photochemical and electrochemical results of studies with cobalt and manganese oxides clearly suggest that these materials hold promise for developing robust, efficient, nanometer-sized catalysts for water oxidation. Herein we report efficient oxygen evolution at nanostructured Co$_3$O$_4$ clusters in mesoporous silica in aqueous solution under mild temperature and pH conditions for the first time. The catalyst was driven by the [Ru$^{2+}$ (bpy)$_3$]/persulfate'sensitizer system under visible light.

Typical TEM images of Co$_3$O$_4$ nanoclusters prepared in SBA-15 silica at 4.2 and 8.6 wt % loading (as determined by inductively coupled plasma mass spectrometer (ICP-MS)) by wet impregnation are shown in FIG. 1$a$,$b$.[12, 20-22] The images show that the integrity of the silica channel structure (diameter 8 nm) was maintained upon formation of the Co$_3$O$_4$ clusters. By examining many SBA-15 particles in different regions of the powder, we confirmed that Co$_3$O$_4$ nanoclusters are formed exclusively inside the mesopores. The spheroid-shaped clusters consist of parallel bundles of nanorods whose structure is imposed by the silica channels. The rods are linked by short bridges, formed by Co$_3$O$_4$ growth in the micropores interconnecting the mesoscale channels.[22] TEM images of the Co$_3$O$_4$ clusters were recorded after removal of the silica scaffold by heating of a suspension of the SBA-15/Co$_3$O4 sample in aqueous NaOH (2 m) at 60° C. for 30 min. As an example, FIG. 1$c$ shows a cluster isolated from the 8% sample. Analysis of numerous clusters shows that for the 4% sample, the average Co$_3$O$_4$ spheroid-shaped bundle has a short diameter of 35 nm and a long diameter of 65 nm (histogram analysis shown in Example 2).[12] For the 8% sample, the average bundle of nanorods makes a spheroid with short and long diameters of 65 and 170 nm, respectively.

Figure 2:
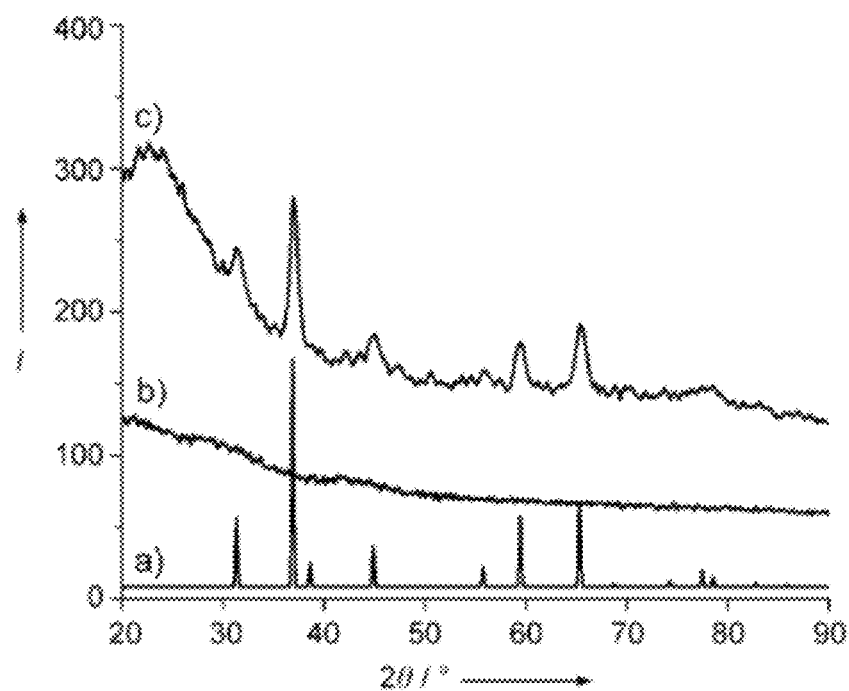
FIG. 2 shows the wide-angle powder XRD patterns for a) micrometer-sized $Co_3O_4$ particles, b) SBA-15/$Co_3O_4$ (4%), c) SBA-15/$Co_3O_4$ (8%).
Figure 3:
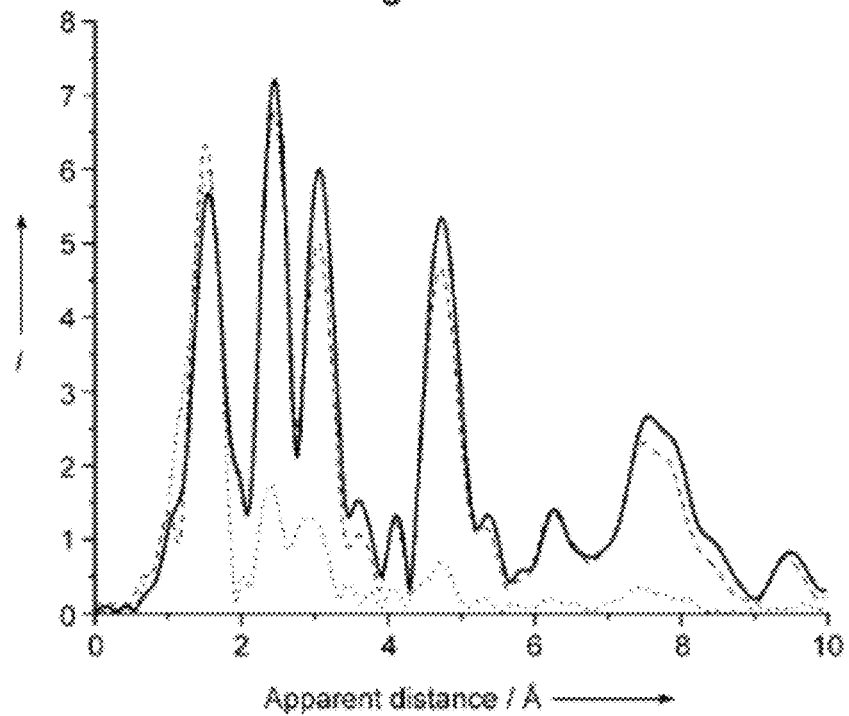
FIG. 3 shows the EXAFS spectra for bulk $Co_3O_4$ (c), SBA-15/$Co_3O_4$ (4%; a), and SBA-15/Co3O4 (8%; b).

Selected area electron diffraction (SAED) images (FIG. 1$b$, inset) confirm the crystalline nature of the large Co$_3$O$_4$ nanoclusters (8% sample). By contrast, no clear diffraction pattern was observed for the 4% sample, suggesting that the 35 nm clusters are poorly crystallized. These findings are confirmed by powder X-ray diffraction (XRD) measurements (FIG. 2). The diffraction peaks of the bulk Co$_3$O$_4$ phase (trace a) are characteristic for Co$_3$O$_4$ (spinel structure). The same peaks are clearly visible in the pattern of the Co$_3$O$_4$ clusters of the 8% sample (trace c) but are absent in the 4% sample (trace b). The absence of diffraction peaks for the 35 nm clusters indicates that the crystalline domains are very small (at most a few nanometers) and points to polycrystallinity. The width of the XRD bands in the case of the 8% sample corresponds to a 7.6 nm object according to the Scherrer formula, in agreement with the expected diameter of Co$_3$O$_4$ nanorods imposed by the SBA-15 channel structure (FIG. 1). Fourier transformed extended X-ray absorption fine structure (EXAFS) data for micrometer-sized Co$_3$O$_4$ particles and Co$_3$O$_4$ nanoclusters of 8% and 4% loaded SBA-15 are shown in FIG. 3. The perfect agreement between the spectra of bulk Co$_3$O4 ( - - - ) and SBA-15/Co$_3$O$_4$ (8%) ( - - - ) confirms the well-crystallized spinel structure of the large clusters, consistent with the SAED and powder XRD results. For the 4% sample ( - - - ), there is good agreement between the first-shell CO—O bond lengths for the nanoclusters and the bulk phase. The higher-shell Co—Co peaks, while clearly visible, have much lower intensity, indicative of very small (few nanometer) crystalline Co$_3$O$_4$ domains within the 35 nm cluster.

Precedents for reduced EXAFS peak intensities arising from polycrystallinity are known.[23] We conclude that the structural characterization reveals spheroid-shaped bundles of parallel $Co_3O_4$ nanorods of spinel structure inside the porous SBA-15 scaffold.

Figure 4:
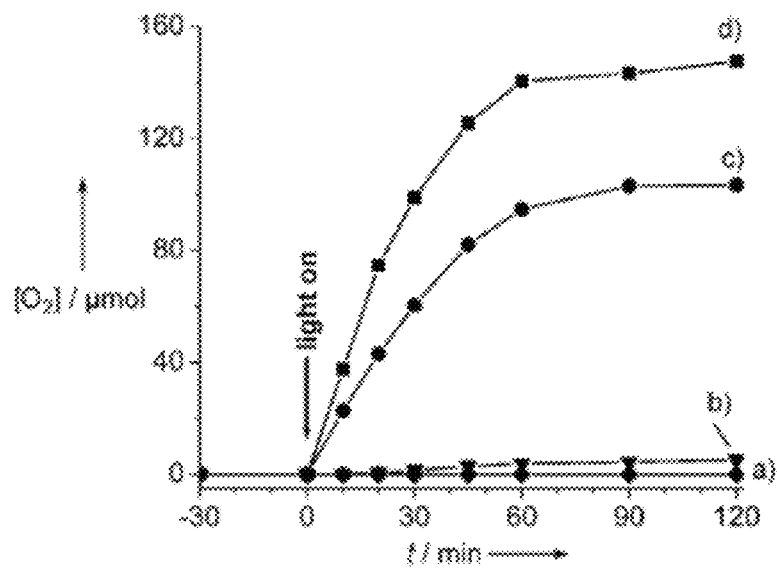
FIG. 4 shows oxygen evolution in aqueous suspensions (40 mL) of: a) SBA-15/NiO (8%), b) micrometer-sized $Co_3O_4$ particles, c) SBA-15/$Co_3O_4$ (8%), and d) SBA-15/$Co_3O_4$ (4%). Measurements were conducted at pH 5.8 and 22° C. Catalysis was initiated by Ar ion laser emission at 476 nm (240 mW). Experimental details of the oxygen detection method are described in Example 2.

Evolution of $O_2$ was observed by mass spectrometric monitoring of the gas in the head space of aqueous suspensions of SBA-15/$Co_3O_4$ catalysts driven by visible light-generated $[Ru^{3+} (bpy)_3]$ at pH 5.8 and room temperature (476 nm, 240 mW; FIG. 4 c, d). A mildly acidic pH value was chosen to minimize photodegradation of the ruthenium complex.[24] The amount of $O_2$ generated increases approximately linearly for the first 30 min before gradually leveling off. When adding fresh $Na_2S_2O_8$ acceptor and readjusting the pH value to 5.8, oxygen evolution resumed at the same rate as observed initially, within uncertainties. This finding confirms that the slowdown of the water oxidation rate is principally due to the stoichiometric consumption of the persulfate acceptor and demonstrates that the activity of the $Co_3O_4$ nanoclusters does not degrade during photocatalysis on the time scale investigated (several hours). X-ray absorption near-edge structure (XANES) and EXAFS analysis of the $Co_3O_4$ clusters before and after photochemical runs did not reveal any structural or oxidation-state changes of the catalyst (see Example 2). [12] NiO was prepared in SBA-15 at the same loading level (8%), and photolysis was conducted under conditions identical to those used for the SBA-15/$Co_3O_4$ samples.[12] As can be seen from FIG. 4 a, no $O_2$ evolution was detected, thus confirming that $Co_3O_4$ nanoclusters are responsible for water oxidation. We conclude that $Co_3O_4$ nanoclusters of spinel structure in SBA-15 silica material exhibit strong oxygen evolution activity under mild pH and temperature conditions at an overpotential of 350 mV ($\epsilon^{\circ}$ ($[Ru^{3+}(bpy)_3]/[Ru^{2+}(bpy)_3]$)=1.24 V, $\epsilon^{\circ}$ ($O_2/H_2O$)=0.89 V at pH 5.8).[25]

While the modest overpotential for driving the catalyst implies reasonable thermodynamic efficiency, the turnover frequency (number of oxygen molecules per second per nanocluster) and size of the catalyst determine the degree to which an integrated system featuring this catalyst will be able to keep up with the rate of incident solar photons. From the amount of $O_2$ gas evolved in the headspace during the first ten minutes of photolysis (FIG. 4), taking into account the equilibrium oxygen concentration in the solution volume,[9] we estimate a TOF=1140 $s^{-1}$ per $Co_3O_4$ nanocluster. The calculation is based on the geometry of the bundles of $Co_3O_4$ nanorods described above (bundle diameter 35 nm, rod diameter 7.6 nm, typically 14 rods per bundle, average rod length 50 nm),[12] the loading of 8.4 mg, and the density of $Co_3O_4$ (6.07 $gcm^{-3}$). We conclude that values for turnover frequency and size of the $Co_3O_4$ nanoclusters on SBA-15 (4% loading) lie in a range adequate for quantitative use of solar photons. For the larger $Co_3O_4$ clusters of the SBA-15/$Co_3O_4$-(8%) catalyst, the estimated TOF is 3450 $s^{-1}$. The calculation assumes $Co_3O_4$ nanorod bundles of spheroid shape (average of 48 nanorods per bundle, rod diameter 7.6 nm, average rod length 130 nm).[12]

As can be seen from FIG. 4, the oxygen yield is 65 times smaller for an aqueous suspension of 200 mg of bare $Co_3O_4$ particles of several-micrometer size (trace b) compared to that of the nanoclusters of SBA-15/$Co_3O_4$ (4%) (containing 8.4 mg $Co_3O_4$) and 40 times smaller compared to the SBA-15/$Co_3O_4$ (8%) sample (containing 17.2 mg $Co_3O_4$). Normalized to the same amount of $Co_3O_4$, the $O_2$ yield for the SBA-15/$Co_3O_4$ (4%) sample exceeds that of the bare micrometer-sized particles by a factor of 1550. Clearly, the interior of the particles or clusters is not involved in the catalysis. On the other hand, assuming the geometry for the particles and nanoclusters described above and taking as nanocluster surface the combined surface area of all nanorods of the bundle (16 percent of the cobalt is at the surface), we calculate that the ratio of the total number of surface Co centers of the $Co_3O_4$ nanocluster sample to micrometer-sized $Co_3O_4$ sample is 96 in the case of SBA-15/$Co_3O_4$ (4%). This result suggests that the much larger surface area provided by the internal nanorod structure of the $Co_3O_4$ clusters is a major factor for the high TOF of the nanoclusters. However, the fact that the estimate based on surface area alone falls short of the observed $O_2$ rate increase suggests that, in addition, Co surface sites of nanoclusters are substantially more efficient catalytically (by a factor of 16) than those of micrometer-sized particles (TOF of 0.01 s!1 per surface Co center for SBA-15/$Co_3O_4$ (4%) sample compared to 0.0006 $s^{-1}$ for micrometer-sized particles). (While we observed a very small amount of oxygen evolution for micrometer-sized $Co_3O_4$ particles upon photolysis using experimental procedures identical to those described in the literature (Ref. [4]), we did not observe the much higher water oxidation rates reported by the previous authors) The lower $O_2$ product yield for SBA-15/$Co_3O_4$ (8%) compared to SBA-15/$Co_3O_4$ (4%) (FIG. 4) despite the two times larger total number of surface Co atoms of the former may signal less efficient access of the reactant to the surface of individual nanorods in the case of the larger nanorod bundles.

The quantum efficiency of the $[Ru^{2+} (bpy)_3]$/persulfate system used herein for driving the water oxidation catalyst is calculated as 18% for the SBA-15/$Co_3O_4$ (4%) experiment (two times the number of $O_2$ molecules produced divided by the number of photons absorbed by the sensitizer).[4] This quantum yield is only a lower limit, because it is assumed that all photons are absorbed by the sensitizer in the strongly scattering suspension, which is an overestimation. The value is influenced by several factors, including the efficiency of electron transfer between the excited $[Ru^{2+} (bpy)_3]$ sensitizer and the $S_2O_8^{2-}$ acceptor and the efficiency of charge transfer between $Co_3O_4$ nanoclusters and $[Ru^{3+} (bpy)_3]$ inside the silica mesopores. Hence, the quantum yield may depend on the particular sensitizer used for driving the catalyst. Note that the turnover frequencies were not limited by the visible light intensity and are therefore intrinsic properties of the $Co_3O_4$ catalysts.

In conclusion, oxygen evolution at nanostructured $Co_3O_4$ clusters in mesoporous silica reported herein constitutes the first observation of efficient water oxidation by a nanometer-sized multielectron catalyst made of a first-row transition-metal oxide. We have previously shown that metal oxide nanocluster catalysts for water oxidation can be driven efficiently by visible-light-absorbing binuclear charge-transfer chromophores,[9] which are of few ångström size. Therefore, rates and size of the catalyst including chromophore are comparable to nature's photosystem II, in which the majority of the space is taken up by the light-harvesting system rather than the catalyst. The abundance of the metal oxide, the stability of the nanoclusters under use, the modest overpotential, and the mild pH and temperature conditions make this a promising catalytic component for developing a viable integrated solar fuel conversion system, the next important challenge in this field.

Experimental Section

The synthesis of the catalysts is described in detail in Example 2. The materials were characterized by transmission electron microscopy (TEM, LIBRA at NCEM), powder X-ray diffraction (PXRD, Siemens model D500 diffractometer equipped with CuKα1 radiation, λ=1.541 Å), and $N_2$ adsorption (Quantachrome Autosorb 1). XANES and EXAFS data were collected at Beam line 7.3 of SSRL. The data were treated by the Ifeffit software. The photolysis experiments were conducted With a continuous visible laser source and mass spectrometric monitoring of oxygen, as described in the Example 2.

EXAMPLE 2

TABLE 1

Turnover frequencies (TOF) for oxygen evolution at Co and Mn oxide materials reported in the literature

| Oxide | TOF$^a$/s$^{-1}$ | Overvoltage, η/mV | pH | T/° C. | Quantum yield |
|---|---|---|---|---|---|
| $Co_3O_4$ | 0.035 | 325 | 5 | RT | 58% |
| $Co_3O_4$ | >0.0025 | 350 | 14 | 30 | — |
| $Co_3O_4$ | >0.020 | 295 | 14 | 120 | — |
| $Co_3O_4$ | >0.0008 | 414 | 14.7 | 25 | — |
| $Co_3O_4$ | >0.006 | 235 | 14 | 25 | — |
| $MnO_2$ | >0.013 | 880 | 7 | 30 | — |
| $Mn_2O_3$ | 0.055 | 325 | 5 | RT | 35% |

$^a$Assuming that all deposited metal centers are involved in the catalysis, lower TOF limits are calculated
(b) Density typical for known Co phosphates were assumed: CRC Handbook of Chemistry and Physics, 56th ed.; Weast, R.C. Editor; CRC Press: Cleveland, 1975; p. B-89.

Synthesis of SBA-15

The synthesis of mesoporous silica SBA-15 has been reported previously by Stucky and co-workers.[Zhao, D. Y.; Feng, J. L.; Huo, Q. S.; Melosh, N.; Fredrickson, G. H.; Chmelka, B. F.; Stucky, G. D. Science 1998, 279, 548.] Briefly, 2 g of poly(ethylene glycol)-block-poly(propylene glycol)-block-poly(ethylene glycol) P123 (average $M_n$~5800, Aldrich) was mixed with 75 mL of water and 4 mL of concentrated HCl (37 wt %, Aldrich) in a beaker, followed by stirring at 40° C. until all polymer was dissolved. Then, 4.4 g of tetraethyl orthosilicate (TEOS, 98%, Aldrich) was added to the solution and stirred at 40° C. for 24 h. The mixture was sealed in an autoclave and heated at 90° C. for another 24 h. After the hydrothermal treatment, the resulting sample was filtered, washed several times with water and dried at 60° C. The polymer template was removed by calcination at 500° C. for 3 h under air.

Synthesis of SBA-15/$Co_3O_4$ and SBA-15/NiO

SBA-15/$Co_3O_4$: $Co_3O_4$ nanoclusters were prepared in the mesoporous silica by the wet impregnation method. [Jiao, F.; Shaju, K. M.; Bruce, P. G. Angew. Chem. Int. Ed 2005, 44, 6550; Tian, B. Z.; Liu, X. Y.; Yang, H. F.; Xie, S. H.; Yu, C. Z.; Tu, B.; Zhao, D. Y., Adv. Mater. 2003, 15, 1370] A typical SBA-15/$Co_3O_4$ with 4% wt $Co_3O_4$ loading described as follows: 0.315 g of $Co(NO_3)_2.6H_2O$ (98%, Aldrich) was dissolved in 50 ml of ethanol followed by addition of 2 g of calcined SBA-15. After stirring the mixture at room temperature until completely dried powder had been obtained, the sample was calcined at 500° C. for 3 h in air, resulting in SBA-15/$Co_3O_4$ with 4% wt $Co_3O_4$ loading. Another SBA-15/$Co_3O_4$ with 8% wt $Co_3O_4$ loading was prepared by using 0.63 g of $Co(NO_3)_2.6H_2O$ precursor through the same approach.

SBA-15/NiO: NiO nanoclusters were prepared in the mesoporous silica by the bi-solvents method. [Tian, B. Z.; Liu, X. Y.; Yang, H. F.; Xie, S. H.; Yu, C. Z.; Tu, B.; Zhao, D. Y., Adv. Mater. 2003, 15, 1370; Jiao, F.; Hill, A. H.; Harrison, A.; Berko, A.; Chadwick, A. V.; Bruce, P. G., J. Am. Chem. Soc. 2008, 130, 5262] A typical SBA-15/$Co_3O_4$ with 8% wt NiO loading described as follows: 2 g of calcined SBA-15 was dispersed in 100 mL of hexane under stirring, followed by addition of 5 mL aqueous solution of 0.677 g of $Ni(NO_3)_2.6H_2O$ (98.5%, Aldrich). After stirring the mixture at room temperature until completely dried powder had been obtained, the sample was calcined at 500° C. for 3 h in air, resulting in SBA-15/NiO with 8% wt NiO loading. ICP-MS analysis of the final products gave actual oxide weight percentages in SBA-15/$Co_3O_4$ (4% loading), SBA-15/$Co_3O_4$ (8% loading), and SBA-15/NiO as 4.2%, 8.6%, 8.3%, respectively.

Figure 5:
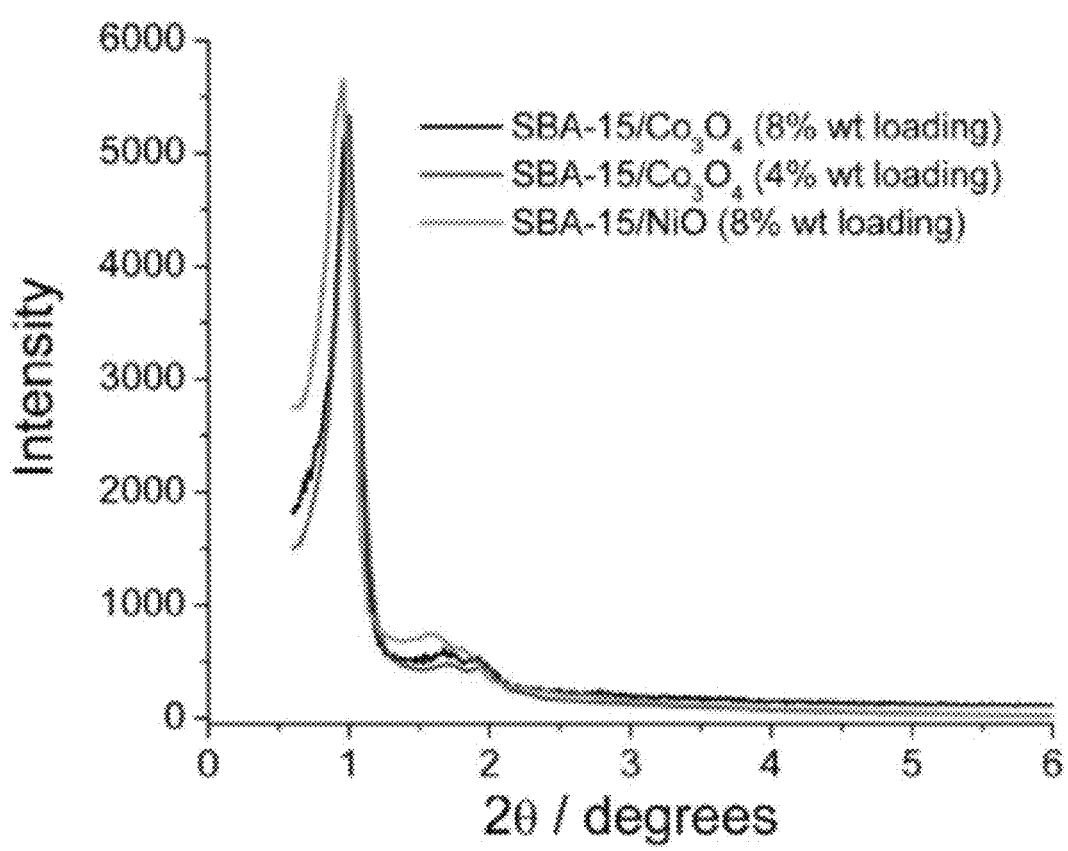
FIG. 5 shows the low-angle PXRD patterns for SBA-15/$Co_3O_4$ and SBA-15/NiO. Low-angle powder XRD measurements confirm that the silica channel structure remains intact upon metal oxide loading.

FIG. 5 shows the low-angle PXRD patterns for SBA-15/$Co_3O_4$ and SBA-15/NiO. Low-angle powder XRD measurements confirm that the silica channel structure remains intact upon metal oxide loading.

Figure 6:
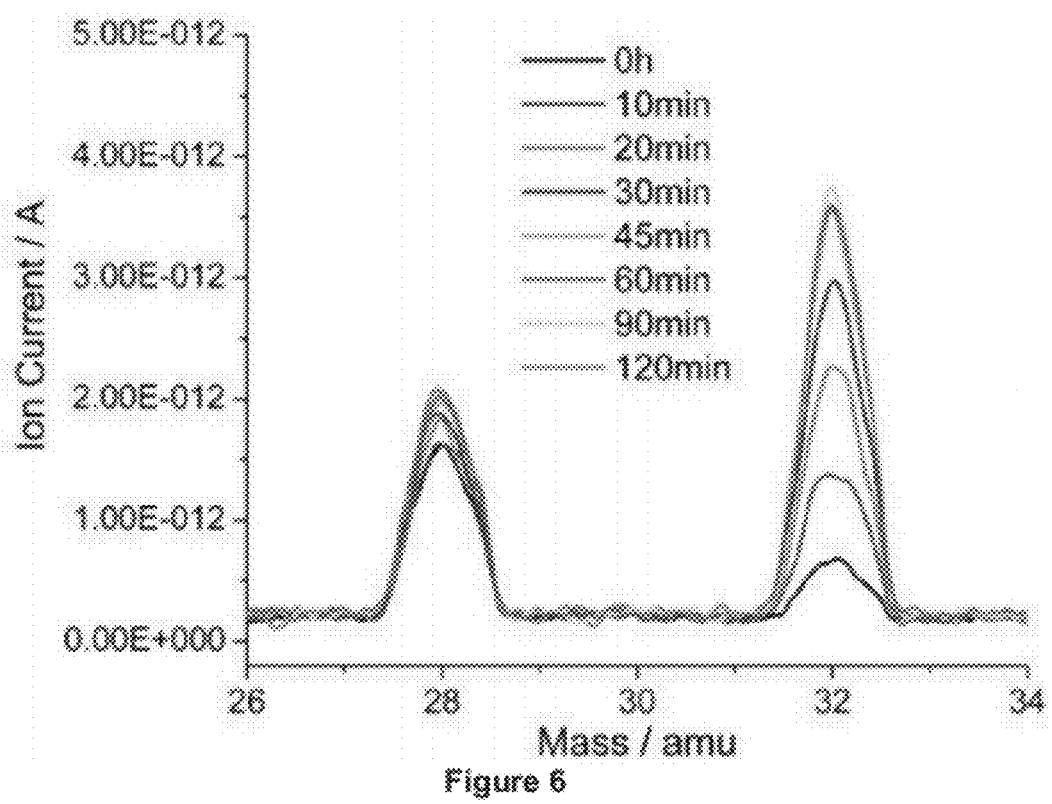
FIG. 6 shows the mass spectra of $O_2$ evolution using SBA-15/Co $Co_3O_4$ 3O4 4% wt loading as a catalyst.

Water Oxidation Experiments:

Photochemical water oxidation experiments were conducted in a 50 mL flask containing 40 mL of aqueous buffer ($Na_2SiF_6$—$NaHCO_3$, 0.022-0.028 M) with pH held at 5.8, 390 mg $Na_2SO_4$, 130 mg $Na_2S_2O_8$, 45 mg [Ru(bpy)3]$Cl_2.6H_2O$, and 200 mg SBA-15/$Co_3O_4$ (4%) (containing 8.4 mg $Co_3O_4$), or 200 mg SBA-15/$Co_3O_4$ (8%)(containing 17.2 mg $Co_3O_4$), or 200 mg μ-sized $Co_3O_4$ particles. The catalyst was degassed in a Schlenk tube under vacuum overnight and refilled with Ar before being transferred into the reactor. The reactor was irradiated with the 476 nm emission line (240 mW) of an Ar ion laser (Coherent model Innova 90-5), with the beam expanded to 1.6 cm diameter. 2.5 mL gas was periodically captured from the headspace of the reactor, followed by direct injection into a quadrupole mass spectrometer (Pfeiffer model Omnistar 422) (FIG. 6). To eliminate any oxygen growth due to a possible air leak, the reactor was maintained in dark for 30 min prior to irradiation, and no oxygen was observed.

FIG. 6 shows the mass spectra of $O_2$ evolution using SBA-15/$Co_3O_4$ 4% wt loading as a catalyst. Growth of mass 32 signal shows $O_2$ evolution. Small increase at mass 28 is due to CO produced by photodegradation of the Ru(bpy)$_3$ sensitizer. Note that the leveling off of the $O_2$ growth is caused by the depletion of the persulfate acceptor (major) and by the decomposition of the Ru sensitizer (minor). The latter is more pronounced for systems with lower rates of $O_2$ formation because the transient oxidized Ru complex is less efficiently removed (i.e. reduced by evolution of oxygen). This is manifested in the lower asymptotic growth limit of $O_2$ for the SBA-15/$Co_3O_4$ (8%) sample compared to the SBA-15/$Co_3O_4$ (4%) sample (FIG. 4).

Figure 7:
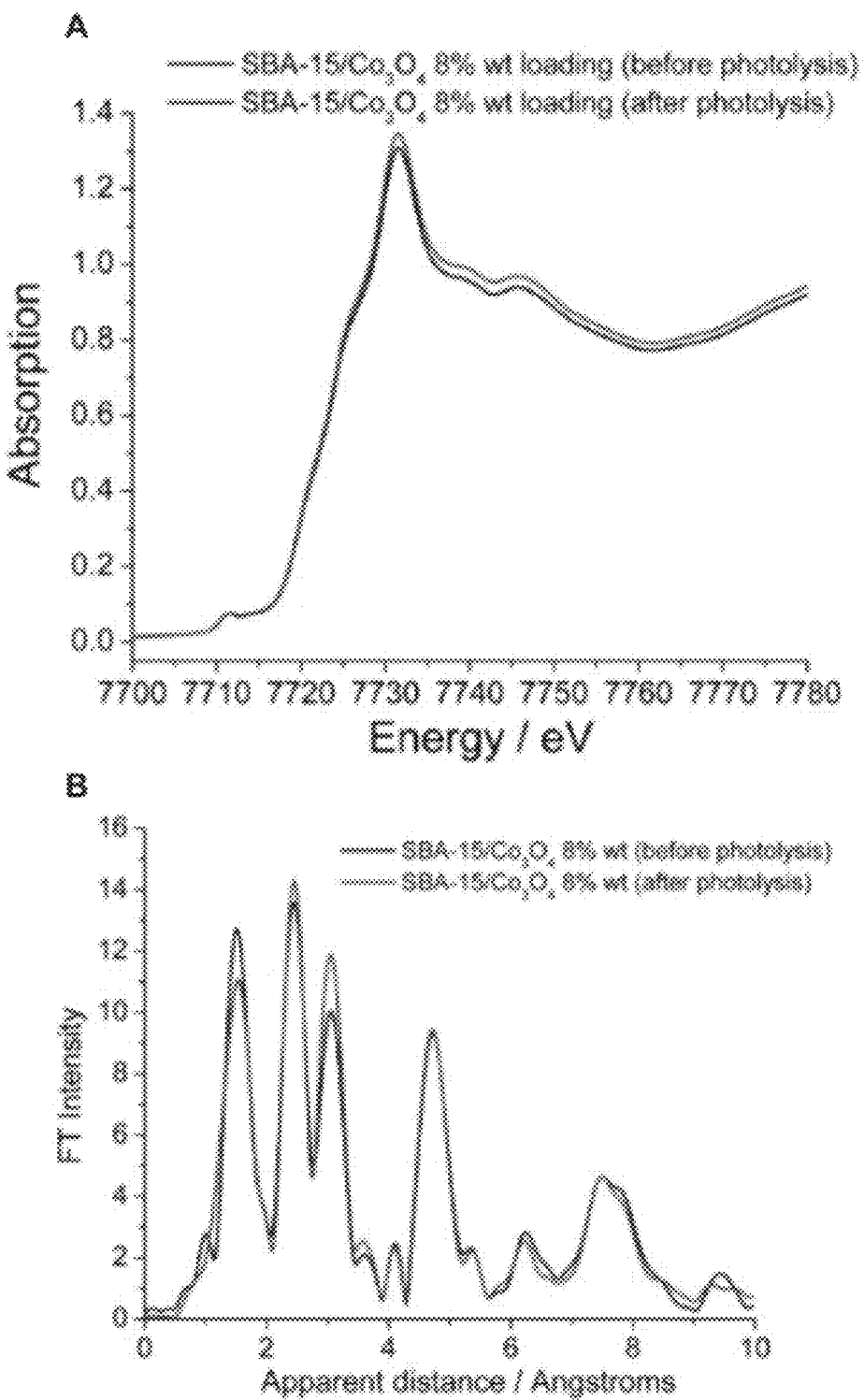
FIGS. 7A and 7B show the XAFS spectra of $Co_3O_4$ catalyst before and after water oxidation experiments.

FIG. 7 shows the XAFS spectra of $Co_3O_4$ catalyst before and after water oxidation experiments Co K edge and EXAFS spectra recorded before and after oxygen evolution in aqueous solution do not exhibit any change of structure or oxidation state of the $Co_3O_4$ nanocluster catalyst. The stability of the Co oxide catalyst was further confirmed by the absence of significant leaching of Co ions during photolysis; ICP-MS analysis of solutions after photolysis contained at most 20 ppm Co ions (0.32 μg mL$_{-1}$). A photochemical experiment with an aqueous solution of such a small amount of Co ions was conducted and no $O_2$ evolution detected.

Figure 8:
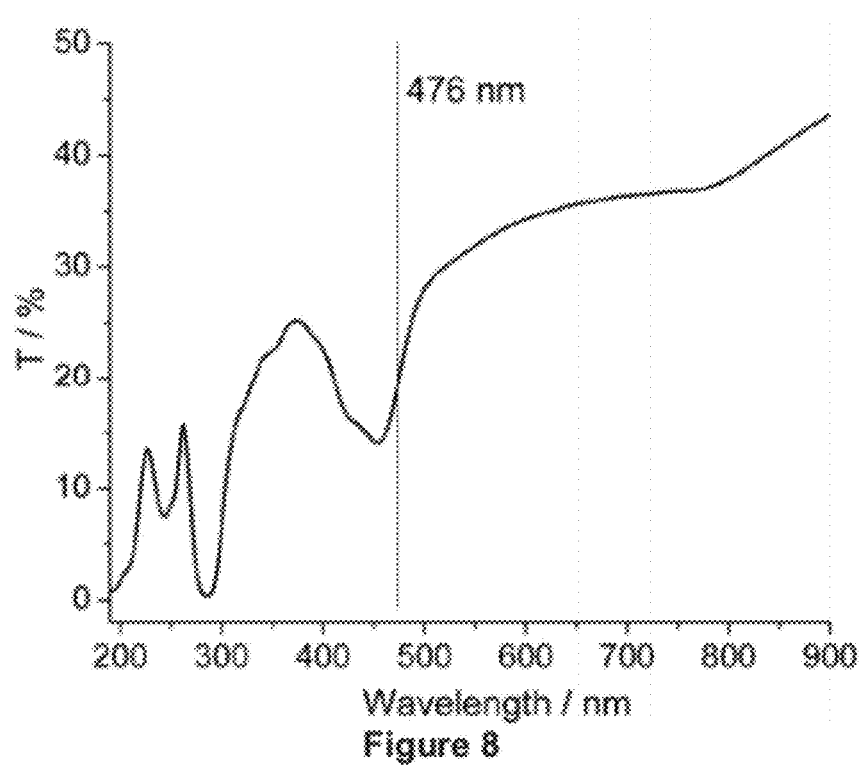
FIG. 8 shows the UV-Vis spectrum of solution before reaction (catalyst: SBA-15/$Co_3O_4$ 8% wt loading).
Figure 9:
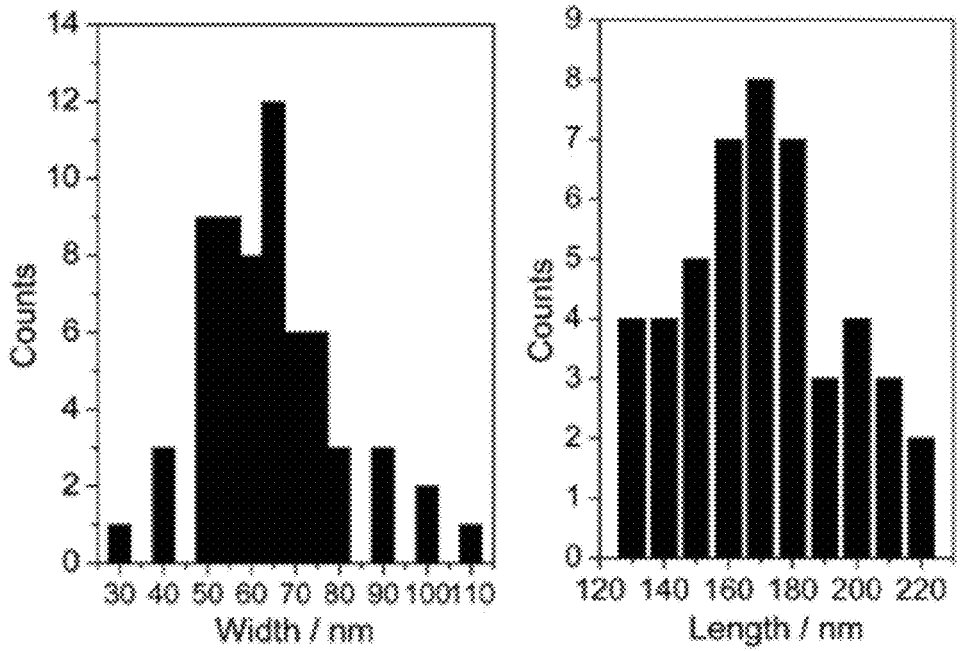
FIG. 9 shows the results of cluster size analysis: dispersion, histogram. The width and length represent the short and the long diameter of the spheroid.
Figure 9:
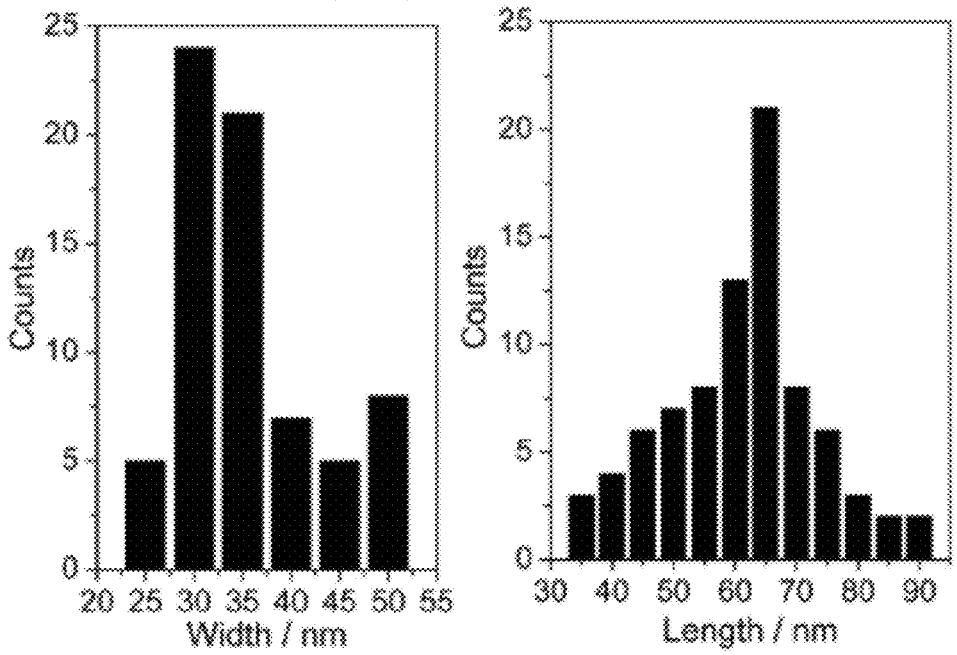

FIG. 8 shows the UV-Vis spectrum of solution before reaction (catalyst: SBA-15/$Co_3O_4$ 8% wt loading). The vertical line indicates the 476 nm emission of the Ar ion laser source.

Nitrogen gas adsorption measurements confirmed that the pore size of the SBA-15 support was maintained after Co oxide loading while the pore volume was reduced by approx. 20 percent. The latter observation is consistent with the formation of metal oxide clusters inside the silica mesopores.

The decrease of the inner surface area upon Co oxide formation was percent nuclear material. No water oxidation was observed in a solution containing $Ru^{+2}(bpy)_3$ sensitizer and persulfate acceptor alone (no SBA-15/$Co_3O_4$ catalyst). In this case, $Ru^{+2}(bpy)_3$ decomposes rapidly as has been reported before (the same process is responsible for the monotonous decrease of the asymptotic $O_2$ product yield with decreasing efficiency of the catalyst because the sensitizer is destroyed more rapidly the slower the catalysis (FIG. 4).

TABLE 2

| Sample | Surface area $m_2/g$ | Pore volume cc/g | Pore size nm |
|---|---|---|---|
| SBA-15 | 878 | 1.16 | 8.2 |
| SBA-15/$Co_3O_4$ 4% loading | 596 | 0.85 | 7.6 |
| SBA-15/$Co_3O_4$ 8% loading | 533 | 0.74 | 7.1 |
| bulk $Co_3O_4$, micron sized | 0.95 | — | — |

Materials: Bulk $Co_3O_4$ (Aldrich, powder, <10 micron).

EXAMPLE 3

Synthesis of nanostructured $Co_3O_4$ and Mn oxide clusters in mesoporous silica scaffolds affords catalysts with very high densities of surface metal sites per projected area, with the silica environment providing stability in terms of dispersion of the clusters and prevention of restructuring of catalytic surface sites. Stacking of the nanoclusters of these earth abundant, durable oxide catalysts in the scaffold results in turnover frequencies per projected area that are sufficient for keeping up with the photon flux at high solar intensity. Opportunities for expanding the metal oxide/silica interface approach to heterogeneous water oxidation catalysis to a more general approach for multi-electron catalyst designs based on core/shell constructs are discussed. The results are reviewed in the context of all-inorganic materials for catalytic water oxidation reported recently from other laboratories, in particular electrodeposits generated from Co phosphate solutions, a molecular water oxidation catalyst based on a polyoxotungstate featuring a Co oxide core, and Mn oxide materials with incorporated Ca ions.

Co and Mn Oxide Nanostructured Clusters in Mesoporous Silica Scaffolds

With some of the Co and Mn oxide materials approaching a lower limit for the TOF of $0.01\ s^{-1}$ per metal center at room temperature according to the electrochemical and photochemical results reviewed above, one might envision highly nanostructured, large surface area particles of these oxides that pack a sufficiently high number of sites to yield kinetically competent catalysts. Nanostructuring may have the additional benefit of enhanced activity per site because metal centers on sharply curved surfaces are likely to be more reactive than on flat surfaces. Moreover, even if such catalytic particles do not yet match the rate of incident solar photons, tens or hundreds of particles can be prepared on a high-surface area, nanostructured inert support like mesoporous silica. In this way, the required TOF of $100\ s^{-1}\ nm^{-2}$ per projected area of the catalyst ensemble may be reached. At the same time, the silica support provides a stable dispersion of the catalyst clusters. Inert nanostructured oxide scaffolds could be used, in addition, for the hierarchical arrangement of light absorbing, charge separating catalytic components to yield a complete solar fuel generator.

Preparation of Catalysts

Figure 10:
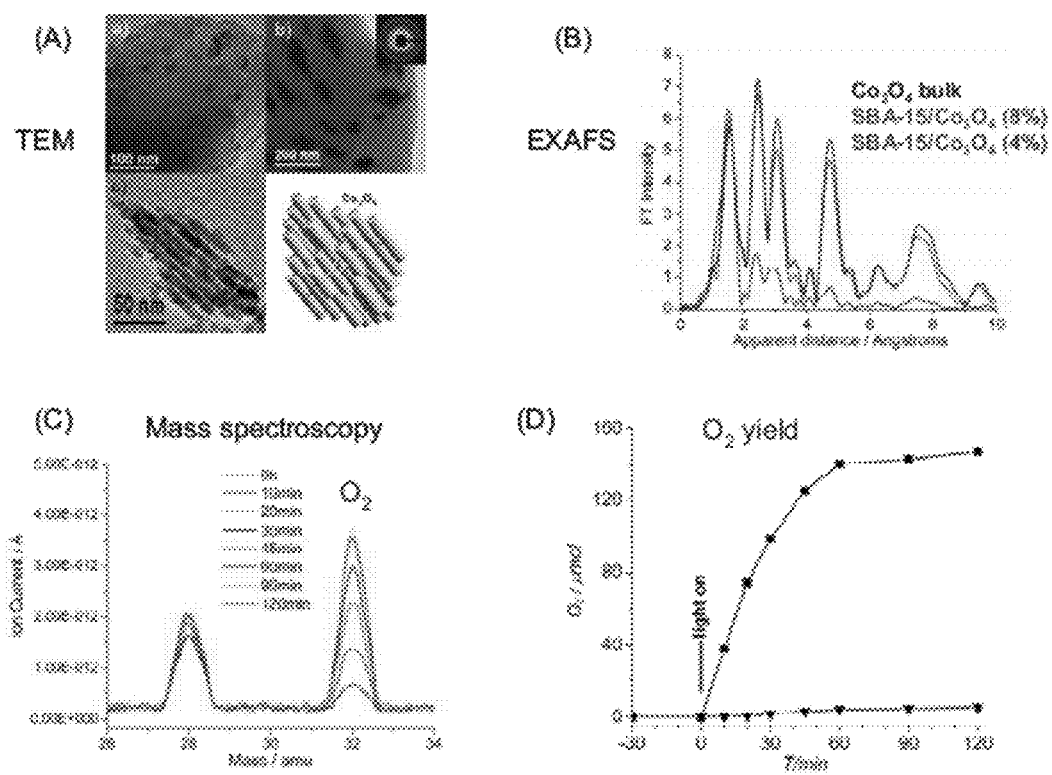
FIG. 10 shows the $Co_3O_4$ nanocluster catalyst for water oxidation in SBA-15 silica support. (A) TEM images of (a) SBA-15/$Co_3O_4$ 4% loading. (b) 8% loading. (c) $Co_3O_4$ nanocluster (8%) after removal of the SBA-15 silica material using aqueous NaOH as edging agent. (B) EXAFS spectra for SBA-15/$Co_3O_4$ samples and comparison with bulk $Co_3O_4$. (C) and (D): Mass spectrometric monitoring of visible light driven oxygen evolution of SBA-15/$Co_3O_4$ (4%) aqueous suspension, and comparison with $Co_3O_4$ micron sized particle suspension.
Figure 12:
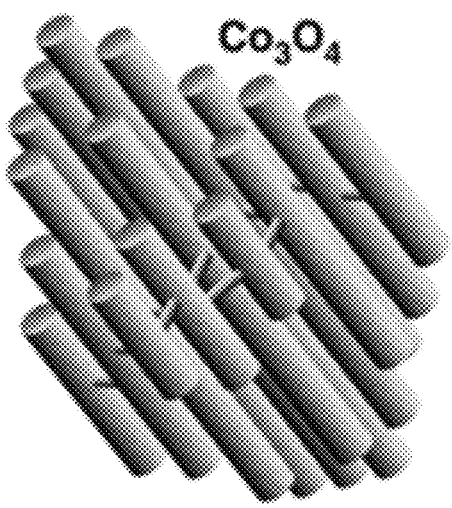
FIG. 12 shows spheroid-shaped Co oxide nanoclusters.

Based on the idea of highly nanostructured catalyst particles of first row transition metals, we have explored the synthesis of Co and Mn oxide clusters inside mesoporous silica supports. The preparation method consists of wet impregnation of the corresponding metal nitrate precursor followed by calcination at carefully chosen temperatures. Spheroid-shaped Co oxide nanoclusters were obtained in SBA-15 as shown in the transmission electron microscopic (TEM) images of FIG. 1. SBA-15 is a mesoporous silica with uni-dimensional channel structure of 8 nm diameter separated by walls of approx. 2 nm thickness. Each cluster is a bundle of parallel nanorods interconnected by small bridges. This is best seen in FIG. 1c, which shows a bare Co oxide cluster after removal of the silica support by etching with concentrated aqueous hydroxide. Close examination of the TEM images reveals that the silica mesopores remain completely intact upon Co oxide growth. Hence, the clusters are replica of the SBA-15 pore structure including the micropores that interconnect the mesoscale channels and give rise to the short bridges between the nanorods (FIG. 12). The mean short diameter of the 4 wt % spheroidal cluster is 35 nm with an average nanorod length of 50 nm, while the corresponding dimensions for the 8 wt % cluster are 65 and 170 nm, respectively. The Co oxide clusters are crystalline with Co3O4 (spinel) structure as confirmed by XRD (FIG. 2) and EXAFS measurements (FIG. 10).

Figure 13:
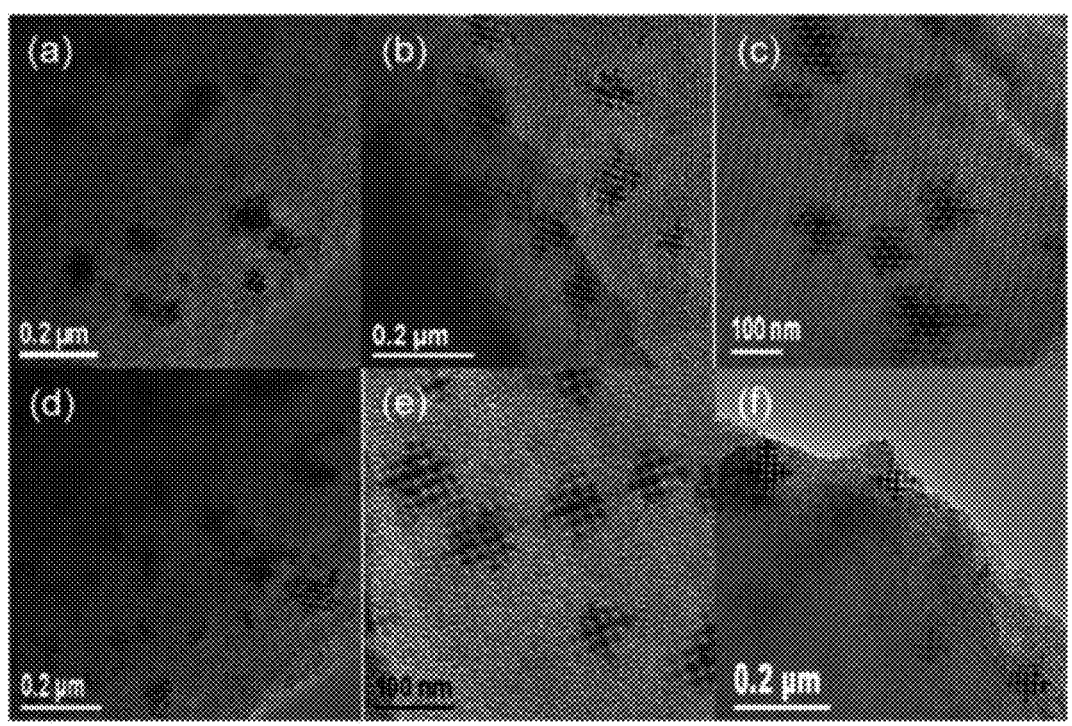
FIG. 13 shows TEMimages for Mn oxide nanoclusters supported on mesoporous silica KIT-6. Calcination treatment: (a) 400° C., (b) 500° C., (c) 600° C., (d) 700° C., (e) 800° C. and (f) 900° C.
Figure 14:
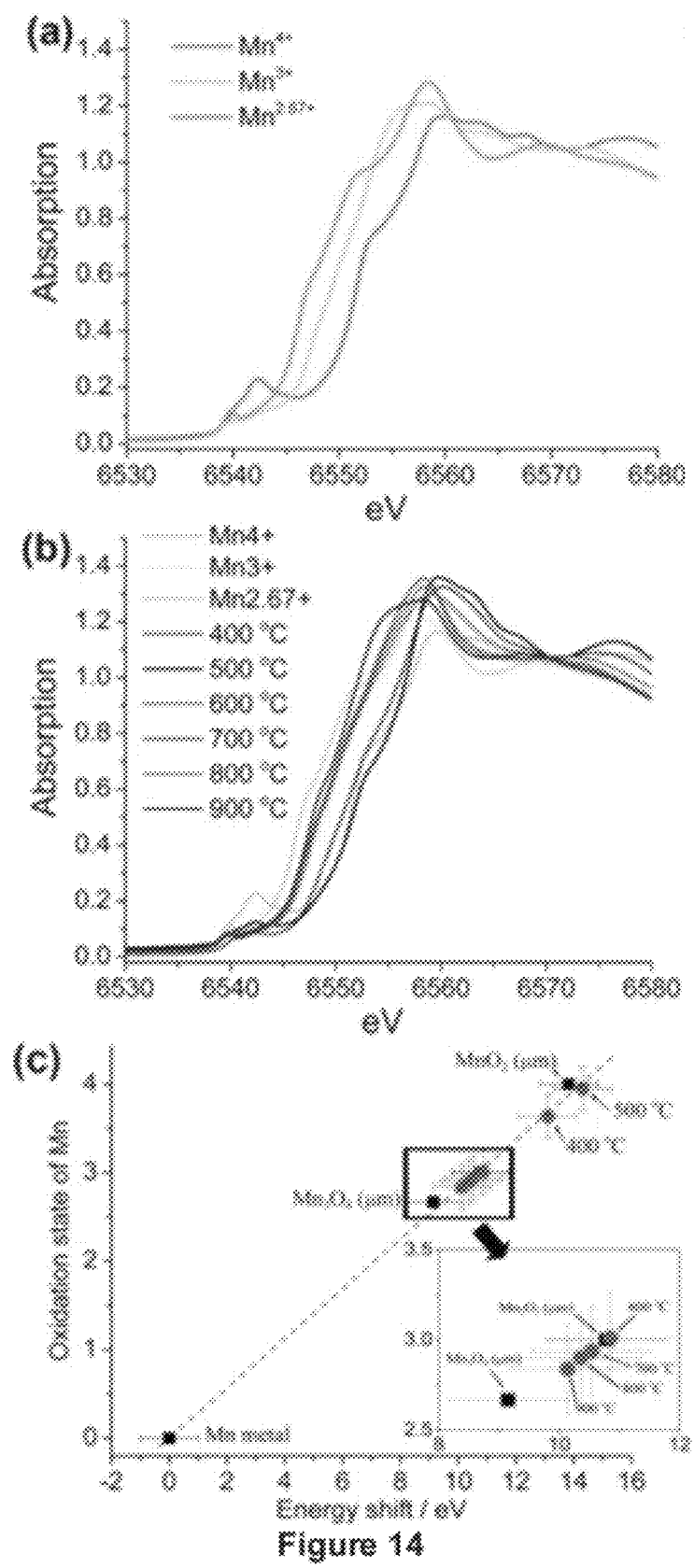
FIG. 14 shows X-Ray absorption measurements of KIT-6/$MnO_x$ samples and reference Mn oxide materials. (a) XANES spectra of micrometer-sized particles of $MnO_2$ (green), $Mn_2O_3$ (yellow), and $Mn_3O_4$ (blue). (b) XANES spectra of KIT-6/Mn oxide materials calcined at temperatures between 400 and 900° C. To facilitate comparison, traces of the reference materials of panel (a) are also shown in faint color. (c) Average oxidation state of Mn for the various KIT-6/Mn oxide samples derived from the K-edge energy

Using a similar procedure, wet impregnation of Mn nitrate in mesoporous silica of a different structure, namely the 3D channel system of KIT-6,57 followed by calcination treatment resulted in spherical nanocluster of 70-90 nm diameter, as shown in TEM images in FIG. 13. In contrast to the case of Co oxide in SBA-15, X-ray absorption spectroscopy revealed that the Mn oxide clusters in KIT-6 have more than one structural phase. Component analysis of X-ray absorption near edge structure (XANES) data is consistent with the presence of $Mn_2O_3$, $MnO_2$, and $Mn_3O_4$ phases, with the composition strongly dependent on the calcination temperature between 400 and 900° C., as shown in FIG. 14 and summarized in Table 3.

Knowledge of the atomic and, hence, electronic structure of the nanoclusters is important for insight into how charge is transported across the particle and available for catalysis at the cluster surface. However, it is the detailed makeup of the sharply curved surface of the Co and Mn oxide nanoclusters, in particular oxidation state, coordination geometry and chemical bonding of adjacent surface metal centers that will determine the catalytic activity. The atomic structure of the interior of the cluster may influence only to a limited extent the configuration of surface functionalities critical for catalytic activity, which is equally influenced by the chemical nature of the interface.

Visible Light-Driven Water Oxidation Catalysis

Co oxide catalyst. In order to facilitate comparison of the activity of different types of water oxidation catalysts driven by visible light sensitizers (supported nanoclusters, molecular catalysts, colloids), the $Ru^{2+}(bpy)_3$/persulfate system has proven particularly useful ($Co^{III}(NH_3)_5Cl^{2+}$ is occasionally used as alternative to $S_2O_8^{2-}$ acceptor). Visible light, typically between 450 and 500 nm excites the $Ru^{2+}$ complex, which is instantly oxidized by the sacrificial acceptor to $Ru^{3+}(bpy)_3$. Upon encounter with metal oxide clusters, this moderate oxidant ($\epsilon°=1.24$ V) pulls electrons one at a time from the catalyst, thereby driving the water oxidation catalysis. Mildly acidic aqueous solutions buffered at pH 5.8 are typically chosen to minimize photodegradation of the sensitizer. Measuring mass spectrometrically the $O_2$ gas buildup in the head space of an aqueous suspension of SBA-15/$Co_3O_4$ particles upon illumination of the sensitizer with visible light (476 nm), product growth as shown in FIG. 4 was obtained.

The leveling off of the oxygen buildup after one hour of photolysis is due to the depletion of persulfate acceptor. Replenishing the solution with acceptor and readjusting the pH to 5.8 (four protons are generated per $O_2$ product molecule, leading to a pH decrease even for the buffered solution to pH 5.1) resulted in continued water oxidation at the original rate indicating undiminished activity of the catalyst. This implies that the photosensitizer is rereduced to the $Ru^{2+}$ state and rules out the possibility that transient $SO_4^-$ ions directly oxidize the Co oxide nanoclusters ($SO_4^-$ does not act as oxidant of the catalyst because the concentration of $Ru(bpy)_3$ sensitizer, with which the radical reacts very efficiently, exceeds that of $Co_3O_4$ nanoclusters by several orders of magnitude). The lack of significant buildup of Co ions in solution and unchanged Co K-edge EXAFS and XANES spectra of the catalyst after hours of photolysis confirmed the structural stability of the SBA-15/$Co_3O_4$ system under use.

The linearity of the $O_2$ buildup over the initial 30 minutes of photolysis and the high reproducibility of the yield when restoring initial acceptor concentration and pH allowed us to assess quantitatively the activity of the $Co_3O_4$ clusters. Based on the size of the nanoclusters from TEM and, hence, the number of clusters contained in the SBA-15/$Co_3O_4$ powder suspended in solution, the TOF per nanocluster could be determined. For the 35 nm diameter clusters (4 wt % sample) the TOF is 1140 $O_2$ molecules $s^{-1}$. The projection of the catalyst on a plane exposed to the sun is 1000 $nm^2$. Hence, the TOF of the $Co_3O_4$ nanocluster in SBA-15 per projected area is approx. 1 $s^{-1}$ $nm^{-2}$. Stacking of one hundred of the catalyst clusters by pressing a powder of SBA-15/$Co_3O_4$ particles into a wafer (thickness approx. 150 mm) provides a catalyst sample with a TOF of 100 $s^{-1}$ $nm^{-2}$, which is the required rate for keeping up with the photon flux at high solar intensity. Thus, the SBA-15 supported $Co_3O_4$ nanoclusters provide for the first time a robust water oxidation catalyst made of an Earth abundant material that is both kinetically and thermodynamically competent (the overvoltage is 350 mV (1.24-0.89 V), $\epsilon^\circ$ ($O_2/H_2O$) at pH 5.8). That is, the TOF per projected area ($nm^2$) of the cluster is sufficiently high so that stacking of about one hundred catalyst clusters results in a TOF for the ensemble that matches the maximum number of incident solar photons per $nm^2$.

Interestingly, with a TOF of 3450 $s^{-1}$ per nanocluster for the larger $Co_3O_4$ clusters of the 8 wt % sample, a somewhat lower TOF per projected area of the catalyst of 0.5 $s^{-1}$ $nm^{-2}$ is obtained. A likely cause for the diminished rate for the larger catalyst clusters is reduced access of water molecules to the innermost portion of the nanorod bundle (about 50 nanorods per bundle for the 8 wt % catalyst compared to just 14 on average for the 4 wt % sample). The water needs to percolate through the molecule-size spaces between the Co oxide and silica wall surface, which may be increasingly difficult as the size of the cluster is increased. Less facile access of the $Ru(bpy)_3$ sensitizer complex to the catalyst cluster surface might also play a role.

In these water oxidation experiments, the TOF was found to be independent of the light intensity used to drive the photosensitizer (240 mW, beam diameter 1.6 cm). This means that the conditions of our experiments are such that the catalyst itself, not the sensitization system, is rate limiting. This is an important criterion because it assures that the reported TOF is an intrinsic property of the Co oxide nanocluster catalyst. The measured quantum efficiency was found to be 18% for the SBA-15/$Co_3O_4$ (4 wt %) sample, a value that is mainly influenced by the efficiency of electron transfer between the excited $Ru2+(bpy)_3$ sensitizer and $S_2O_8^{2-}$ acceptor, and the efficiency of charge transfer between the $Co_3O_4$ nanoclusters and the $Ru^{3+}$ $(bpy)_3$ species inside the silica nanopores. While the TOF per projected area is a critical performance measure when evaluating and comparing multielectron catalysts for water oxidation, the solar quantum efficiency will become an important performance parameter once the catalyst is integrated into a complete artificial photosynthetic system.

To gain insight into the factors responsible for the high water oxidation activity of the silica supported nanoclusters, in particular the influence of the $SiO_2$ environment, it would be interesting to compare the activity of the SBA-15/$Co_3O_4$ catalyst with a sample of bare clusters devoid of the silica scaffold. While we have been able to remove the silica by hydrogen fluoride etching for imaging (FIG. 1c), such a comparison of the catalytic activity is not feasible because the bare clusters, no longer stably dispersed by the mesoporous support, flock together. Furthermore, the Co oxide surface is likely substantially altered by the treatment with hot alkaline solution. However, comparison of the TOF of the nanostructured $Co_3O_4$ clusters on SBA-15 with that of much larger, mm sized bare $Co_3O_4$ particles provides insight into the factors responsible for the high water oxidation activity of the silica supported nanoclusters. The growth curves (b) and (d) of FIG. 4 reveal that the $O_2$ yield per second is 1550 times larger for 35 nm diameter nanorod bundle in SBA-15 than for micron size $Co_3O_4$ particles, if normalized to equal weight. The yield difference is accounted for mainly by the much larger geometrical surface area of the nanostructured catalyst compared to the micron sized particle; the nanorod bundle catalyst has a 96 times more surface Co centers than the macroscopic particle. The additional factor of 16 signals higher activity of Co centers at the sharply curved surface of the 8 nm diameter nanorods compared to Co on a flat surface.

In a recent detailed study, Tilley and Bell (A. J. Esswein, M. J. McMurdo, P. N. Ross, A. T. Bell and T. D. Tilley, J. Phys. Chem. C, 2009, 113, 15068) have investigated the relationship between the catalytic water oxidation activity of cubic $Co_3O_4$ nanocrystals and their size, covering the range from 5 to 50 nm. When loading the nanocrystals on Ni foam anodes, current measurements in alkaline aqueous solution showed a strictly linear dependence on the accessible surface area. The turnover frequency was 0.12 $s^{-1}$ per Co surface site of the cobalt oxide nanocubes at pH 14. The result lends support to our assumption of a linear dependence of the catalyst activity on the geometrical surface area of the catalyst particle in the case of $Co_3O_4$ nanoclusters in silica scaffolds.

It is interesting to note that rate and size of the nanorod bundle catalyst SBA-15/$Co_3O_4$ (4 wt %) including the (molecular) visible light sensitizer are comparable to Nature's Photosystem II where most space is taken up by the light harvesting system rather than the catalyst. What matters in terms of integrated systems design are speed and space, and the natural photocatalyst and the photosensitized $Co_3O_4$ nanocluster, while completely different designs end up approximately the same in terms of these two critical parameters.

Mn Oxide Catalyst.

Figure 15:
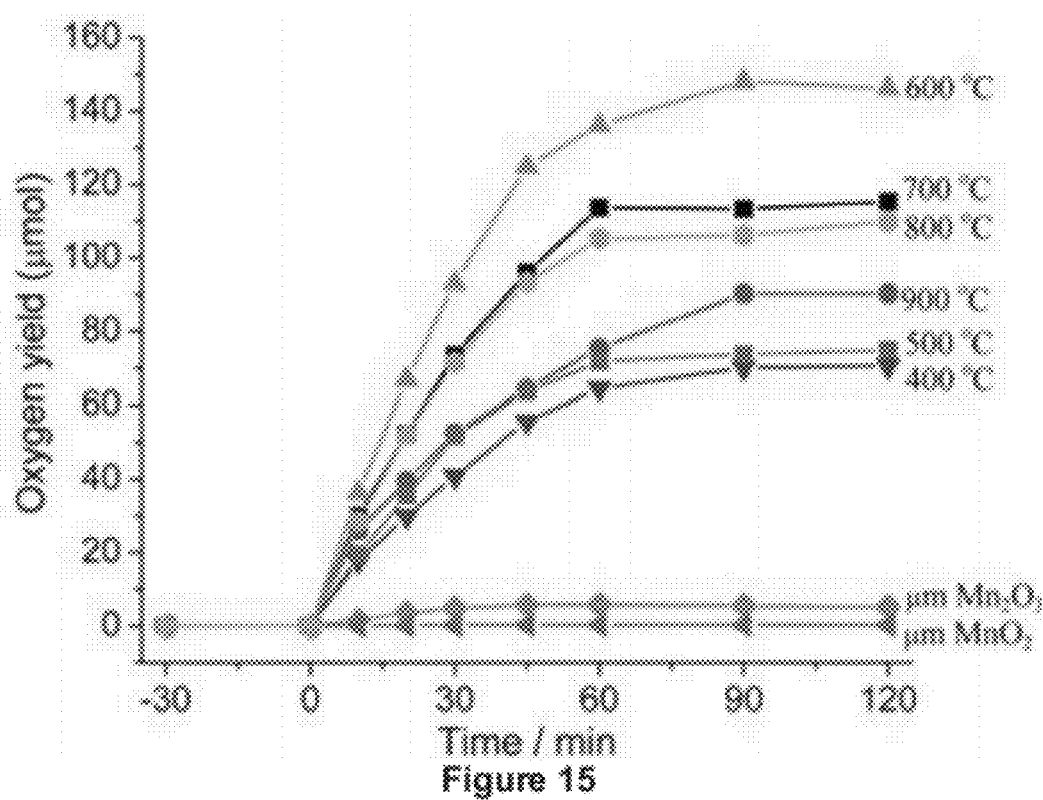
FIG. 15 shows oxygen evolution in aqueous suspension of KIT-6/Mn oxide using the $Ru^{2+}$ $(bpy)_3$-persulfate visible light sensitization system (476 nm, 240 mW), conducted at pH 5.8 and 22° C. Measurements of KIT-6/Mn oxide samples prepared by calcination in the range 400 to 900° C. are shown. For comparison, $O_2$ yields are shown for micrometer sized $Mn_2O_3$ and $MnO_2$ particles (samples with same Mn content).

Using the same visible light sensitization method and mass spectrometric detection of gaseous $O_2$ for the KIT-6/Mn oxide catalyst, the product growth behavior shown in FIG. 15 was observed for samples prepared at the various calcinations temperatures. As in the case of the Co oxide experiments, the oxygen yield was close to linear as function of photolysis time up to the point where persulfate depletion became significant. The high reproducibility of the growth when replenishing the acceptor confirmed the stability of the Mn oxide nanocluster catalysts and allowed us to quantify the activity. For the most active catalyst (calcination at 600° C., composition $Mn_2O_3$ (80%), $MnO_2$ (14%), $Mn_3O_4$ (6%)), a TOF of 3330 $O_2$ molecules s$^{-1}$ per catalyst cluster was obtained. This corresponds to a TOF of 0.6 s$^{-1}$ nm$^{-2}$ projected area of the catalyst, lower but still within less than a factor of two of the activity of the SBA-15/$Co_3O_4$ catalyst. Stacking of between one and two hundred of the Mn oxide nanoclusters in a KIT-6 scaffold meets the kinetic requirement of 100 s$^{-1}$ nm$^{-2}$ under maximum solar flux.

What is particularly remarkable is the structural stability of the Mn oxide nanocluster catalyst after hours of photocatalytic water oxidation, as confirmed by Mn K edge XANES spectroscopy of the catalyst samples and ICP analysis of the reaction solution after photolysis. Nanostructured catalysts, in general, are prone to deactivation by surface restructuring during reaction, yet this seems not to occur for the Co or Mn oxide nanoclusters inside the mesoporous silica scaffold. We speculate that the silica environment prevents restructuring of the nanocluster surface thereby preserving the catalytically active sites. Furthermore, interaction of siloxy, silanol, or siloxane oxygens with the metal oxide surface may suppress leaching of metal centers that otherwise might be labile. It is also possible that specific silica-metal oxide surface interactions play a mechanistic role in the water oxidation catalysis. A further important role of the silica nanopore environment may be its proton permeability, offering paths for proton escape through the nanometer-thin walls. As a result, low proton concentrations are maintained at the catalyst surface which otherwise might increase and suppress the catalytic half reaction. While nanostructuring of Mn and Co oxide catalysts is an important step towards increasing the TOF by increasing the density of catalytic sites, the nature of the catalyst interface with the environment, silica walls in our case, may be equally critical for sustained high activity and durability.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising a nanocluster consisting of a nanostructured transition metal oxide consisting of at least one of cobalt, iron, manganese, niobium, tungsten, or a mixture of two or more of said metals wherein said transition metal oxide is capable of oxidizing two H20 molecules to obtain four protons, and a porous matrix wherein the nanostructured transition metal oxide is embedded on and/or in the porous matrix.

2. The composition of claim 1, wherein the nanostructure is a nanorod.

3. The composition of claim 2, wherein the nanostructure is a nanorod and the nanocluster comprises a bundle of parallel nanorods.

4. The composition of claim 3, wherein two or more nanorods of the bundle of parallel nanorods are interconnected to each other by one or more short bridges.

5. The composition of claim 2 or 3, wherein each nanorod has a diameter of from about 6 nm to about 10 nm.

6. The composition of claim 2 or 3, wherein the length of each nanorods is from about 40 nm to about 60 nm.

7. The composition of claim 3, wherein the nanocluster has a crystalline nature.

8. The composition of claim 1, wherein the transition metal oxide is $Co_3O_4$, $MnO_2$, $Mn_2O_3$, or $Mn_3O_4$.

9. The composition of claim 1, wherein the porous matrix is a mesoporous scaffold.

10. The composition of claim 9, wherein the mesoporous scaffold is a mesoporous silica scaffold.

11. The composition of claim 9, wherein the porous matrix comprises a KIT-6 nanopore or SBA-15.

12. The composition of claim 1, wherein the composition catalyzes the reaction:

$$CO_2 + H_2O \rightarrow CH_3OHO_2$$

visible light,
with a turnover frequency (TOF) equal to or more than 1,000 s$^{-1}$ per nanocluster.

13. The composition of claim 12, wherein the TOF is equal to or more than 1,140 s$^{-1}$ per nanocluster.

* * * * *